United States Patent [19]
Meaney et al.

[11] Patent Number: 5,841,288
[45] Date of Patent: Nov. 24, 1998

[54] TWO-DIMENSIONAL MICROWAVE IMAGING APPARATUS AND METHODS

[75] Inventors: Paul M. Meaney, Windsor, Vt.; Keith D. Paulsen, Hanover, N.H.

[73] Assignee: Microwave Imaging System Technologies, Inc., Hanover, N.H.

[21] Appl. No.: 798,885

[22] Filed: Feb. 11, 1997

Related U.S. Application Data

[60] Provisional application No. 60/011,520, Feb. 12, 1996.

[51] Int. Cl.$^6$ .............................. G01N 22/00; G01R 29/08
[52] U.S. Cl. ......................... 324/639; 324/637; 600/407; 600/430
[58] Field of Search ..................................... 324/632, 637, 324/639, 641, 647, 72; 600/407, 430

[56] References Cited

U.S. PATENT DOCUMENTS

| | | | |
|---|---|---|---|
| 4,135,131 | 1/1979 | Larsen et al. | 3214/615 |
| 4,975,968 | 12/1990 | Yukl | 324/647 X |
| 5,251,645 | 10/1993 | Fenn | 600/407 |

OTHER PUBLICATIONS

Meaney et al., "Microwave Thermal Imaging Using A Hybrid Element Method With A Dual Mesh Scheme For Reduced Computation Time", IEEE Engineering In Medicine And Biology Society (1993), pp. 96–97 (Month unavailable).

Meaney et al., "Finite Element Methods In Impedance Tomography And Microwave Imaging", IEEE Annual Northeast Bioengineering Conference (1993), 25–27, (Month unavailable).

Lynch et al., "Finite Element Solution Of Maxwell's Equations For Hyperthermia Treatment Planning", Journal Of Computational Physics, vol. 58, No. 2 (Apr. 1985), pp. 246–269.

Paulsen et al., "Memory And Operations Count Scaling Of Coupled Finite–Element And Boundary–Element Systems of Equations", International Journal For Numerical Methods In Engineering, vol. 33, (1992), pp. 1289–1303, (Month unavailable).

Lynch et al., "Hybrid Element Method For Unbounded Electromagnetic Problems in Hyperthermia", International Journal For Numerical Methods In Engineering, vol. 23, (1986), pp. 1915–1937, (Month unavailable).

Schwan et al., "Capacity And Conductivity Of Body Tissues At Ultrahigh Frequencies", proceedings Of The I.R.E., vol. 41, pp. 1735–1740 (1953). (Month unavailable).

(List continued on next page.)

*Primary Examiner*—Glenn W. Brown
*Attorney, Agent, or Firm*—Curtis A. Vock

[57] ABSTRACT

The invention provides apparatus and methods for determining electric field properties of an inhomogeneous target. The electric property distribution on a coarse mesh discretization of the target is first estimated; and then the electric field on a fine mesh discretization of the target is computed. The fine mesh has finer discretization than the coarse mesh and is overlapping with the coarse mesh. The electric field is then measured at preselected measurement sites within a homogeneous region external to the target. A Jacobian matrix is also calculated which represents a sensitivity calculation relative to a change in the electric field at selected measurement sites due to a perturbation in the electric property distribution on the coarse mesh. A difference vector is formed between the computed electric field and the measured electric field, and an update vector is added to the electrical property distribution as a function of the difference vector and the Jacobian matrix. The electric field is then re-computed based on the updated electric property distribution, which is compared with the measured electric field to produce a least squared error. If this error is not sufficiently small, the steps above, beginning with computing a Jacobian matrix, are repeated until the error is sufficiently small.

32 Claims, 12 Drawing Sheets

OTHER PUBLICATIONS

Bottomley et al., "*RF Magnetic Field Penetration, Phase Shift And Power Dissipation In Biological Tissue: Implications For NMR Imaging*", Phys. Med. Biol., vol. 23, pp. 630–643 (1978), (Month unavailable).

Burdette et al., "*In situ Permittivity Of Canine Brain: Regional Variations And Post–Mortem Changes*", IEEE Transactions On Microwave Theory And Techniques, vol. 34, pp. 38–49 (1986), Jan.

Jofre et al., "*Medical Imaging With A Microwave Tomographic Scanner*", IEEE Transactions On Biomedical Engineering, vol. 37, pp. 303–312 (1990), Mar.

Rius et al., "*Planar And Cylindrical Active Microwave Temperature Imaging: Numerical Simulations*", IEEE Transactions On Medical Imaging, vol. 11, pp. 457–469 (Dec.).

Miyakawa, "*Tomographic Measurement Of Temperature Change In Phantoms Of The Human Body By Chirp Radar–Type Microwave Computed Tomography*", Med. Biol. Eng. Computat., vol. 31, pp. S31–S36 (1993), Jul.

Bolomey et al., "*Non–Invasive Control of Hyperthermia, Methods Of Hyperthermia Control*", Berlin, Heidelberg, Splinger–Verlag, pp. 35–111 (1990). (Month unavailable).

Paulsen et al., "*Temperature Field Estimation Using Electrical Impedance Profiling Methods: I. Reconstruction Algorithm And Simulated Results*", International Journal of Hyperthermia, vol. 10, pp. 209–288 (1994). (Month unavailable).

Broquetas et al., "*Cylindrical Geometry: A Further Step In Active Microwave Tomography*", IEEE Transactions On Microwave Theory And Techniques, vol. 39, pp. 836–844 (1991), May.

Slaney et al., "Limitations Of Imaging With First–Order Diffraction Tomography", IEEE Transactions On Microwave Theory And Techniques, vol. 32, pp. 860–874 (1984), Aug.

Mallorqui et al., "*Noninvasive Active Microwave Thermometry With A Microwave Tomographic Scanner In Hyperthermia Treatments*", ACES Special Issue On Bioelectromagnetic Computations, AHJ Fleming and KH Joyner (Eds.), ACES Journal, vol. 7, pp. 121–127 (1992). Month unavailable).

TWO-DIMENSIONAL MICROWAVE IMAGING APPARATUS AND METHODS

GOVERNMENT SUPPORT

This invention was made in part with government support under contract number R01-CA55034 awarded by the National Institute of Health. The government has certain rights in the invention.

RELATED APPLICATIONS

This application is a continuation in part of U.S. Provisional application Ser. No. 60/011,520, filed on Feb. 12, 1996, and entitled "Two-Dimensional Microwave Imaging Apparatus," and is hereby expressly incorporated herein by reference.

This application contains, for disclosure purposes, subject matter in the form of a microfiche appendix consisting of four microfiche slides with three-hundred twenty-five frames. The microfiche appendix sets forth non-limiting text and mathematics which are suitable for application with the invention.

FIELD OF THE INVENTION

The invention relates to microwave imaging, and in particular it relates to electromagnetic imaging to reconstruct dielectric properties of inhomogeneous, lossy bodies with arbitrary shape.

BACKGROUND OF THE INVENTION

Microwave imaging of biological bodies has been of interest for a number of years. It was initially viewed as low-cost alternative to computerized tomography ("CT") and has emerged as a modality with potential in several specialty applications. For example, it has been shown that the dielectric properties of biological tissue vary with temperature. See, Schwan et al., *Capacity and Conductivity of Body Tissues at Ultrahigh Frequencies*, Proceedings of IRE, vol. 41, pp. 1735–30 (1953); Bottomley et al., *RF Magnetic Field Penetration, Phase Shift and Power Dissipation in Biological Tissue: Implications for NMR Imaging*, Phys. Med. Biol., vol 23, pp.630–43 (1978); and Burdette et al., *In situ Permittivity of Canine Brain: Regional Variations and Post-Mortem Changes*," IEEE Transactions on Microwave Theory and Techniques, vol. 34, pp.38–50 (1986). Accordingly, a microwave imaging system which monitors dielectric properties can also determine temperature distributions in biological tissue, which might advance the hyperthermia treatment of cancer. See, Jofre et al., *Medical Imaging with a Microwave Tomographic Scanner*, IEEE Transactions on Biomedical Engineering, vol 37, pp.303–312 (1990); Rius et al., *Planar and Cylindrical Active Microwave Temperature Imaging: Numerical Simulations*, IEEE Transactions on Medical Imaging, vol 11, pp.457–469 (1992); and Miyakawa, *Tomographic measurement of temperature change in phantoms of the human body by chirp radar-type microwave computed tomography*, Med. Biol. Eng. Computat., vol 31, pp.531–536 (1993).

However, one problem in applying microwave imaging within therapeutic processes is that it is difficult to monitor temperature distributions throughout the target region since these distributions are needed for both treatment assessment and control. See, Bolomey et al., *Non-invasive Control of Hyperthermia*, Methods of Hyperthermia Control, Berlin, Heidelberg, Splinger-Verlag (1990); Paulsen et al., *Temperature Field Estimation Using Electrical Impedance Profiling Methods: I. Reconstruction Algorithm and Simulated Results*, International Journal of Hyperthermia, vol 10, pp. 209–228 (1994). Accordingly, the prior art has attempted to first generate static microwave images, and then to generate dynamic microwave images which yield data on changes in the temperature field distribution.

Prior art systems used to image biological tissues with active microwave imaging have had mixed results. One system, for example, described in Jofre et al., *Medical Imaging with a Microwave Tomographic Scanner*, IEEE Transactions on Biomedical Engineering, vol 37, pp.303–312 (1990) and Broquetas et al., *Cylindrical Geometry: A Further Step in Active Microwave Tomography*, IEEE Transactions on Microwave Theory and Techniques, vol 39, pp.836–844 (1991), performs microwave imaging at 2.45 GHz. Although this system has shown some promise, especially in the area of differential imaging, it has difficulty in detecting the large electrical property contrasts that naturally occur in biological tissue; and there are other difficulties in resolving both the resistive and reactive components of the electrical property distributions. These problems are due, in part, to the use of the Born approximation during image reconstruction. See, Slaney et al., Limitations of Imaging with First-Order Diffraction Tomography, IEEE Transactions on Microwave Theory and Techniques, vol 32, pp. 860–974 (1984).

A similar system in the prior art utilizes conventional x-ray CT reconstruction algorithms by discriminating the straight line from multipath microwave signals (1–2 GHz) received through chirp-radar techniques, achieving spatial resolutions on the order of 1 cm for static targets. See, Miyakawa, *Tomographic measurement of temperature range in phantoms of the human body by chirp radar-type microwave computed tomography*, Med. Biol. Eng. Computat., vol 31, pp. 531–536 (1993).

Imaging of temperature changes in laboratory phantoms has also been reported, in the prior art, by using differencing methods, although without quantitative measurements of actual temperature changes. See, e.g., Mallorqui et al., *Noninvasive active microwave thermometry with a microwave tomographic scanner in hyperthermia treatments*, ACES Special Issue on Bioelectromagnetic Computations, A H J Fleming and K H Joyner (Eds.), ACES Journal, vol 7, pp. 121–127 (1992).

Prior art microwave imaging systems thus illustrate a general failure in the integration of data acquisition hardware and reconstruction algorithms to produce actual biomedical images. Further, the ability to simultaneously recover absolute and quantitative values for both the resistive and reactive components of the imaged electrical properties has remained elusive.

It is, therefore, one object of the invention to provide microwave imaging apparatus which overcomes many of the problems in the prior art.

Another object of the invention is to provide a microwave imaging system with a reconstruction algorithm for reconstructing the dielectric properties of inhomogeneous, lossy bodies with arbitrary shape.

These and other objects of the invention will be apparent from the description which follows.

SUMMARY OF THE INVENTION

In one aspect, the invention provides a method of determining electric properties of an inhomogeneous target. The method of this aspect includes measuring the electric field exterior to a boundary defining the target and estimating electric property distributions on a coarse mesh discretization of the target. The method of this aspect further includes computing an electric field on a fine mesh discretization of the target, where the fine mesh has finer discretization than the coarse mesh and is overlapping with the coarse mesh, and at points within the homogeneous region.

Preferably, the step of computing of the electric field within the homogeneous region is facilitated by modeling the region by a boundary element representation. Also, the measurement of the electric field typically involves measuring the electric field very near to the boundary and at points within a substantially homogenous region surrounding the target.

In another aspect, the method includes comparing the measured electric field with the computed electric field to determine a difference between measured and computed fields. This difference is compared against a predetermined accuracy to determine whether to perturb the electric property distribution and to repeat the steps to achieve the desired accuracy.

In another aspect, the method includes the step of calculating an update vector involving a Jacobian matrix if the difference exceeds the predetermined accuracy. The Jacobian matrix forms a sensitivity calculation relative to a change in the electric field on the fine mesh due to a perturbation in the electric property distributions on the coarse mesh.

The step of calculating an update vector to the electrical property distribution can include the steps of forming a difference vector between the computed electric field and the measured electric field, and of computing the Jacobian matrix and of solving the set of simultaneous equations defined by (a) the Jacobian matrix and (b) the difference vector between the computed and measured electric fields.

The method typically includes the steps of updating the electric property distribution with the update vector and re-calculating the electric field based upon the new distribution.

In another aspect, the method includes comparing the measured and electric field by computing a least squares error. If this error is not sufficiently small, the previous steps are repeated until an acceptable error is achieved.

In another aspect of the invention, the step of determining the electric fields includes representing a region outside of the target with a homogeneous boundary element representation; representing the target as a plurality of inhomogeneous finite element representations; and coupling the boundary element and finite element representations at the boundary to determine the electric fields within the target and in the homogeneous region.

In yet another aspect, the step of measuring the electric field includes the steps of calibrating the measured electric field by (a) calculating a phase center of each antenna used to transmit an electromagnetic signal, and (b) modifying electric field amplitudes so as to convert the 3-D data to a 2-D data format. The step of calibrating the measured electric field can thus include compensating the 3-D illumination pattern generated by the transmitting antenna as a function of "R," where R is the distance between the transmitting antenna's phase center and each of the receiving antennas. Specifically, the 3-D data is functionally dependent upon $1/R^2$ while the resulting 2-D data format is functionally dependent upon 1/R; and the calibration routine makes this conversion.

In another aspect, the step of calculating the phase center of each antenna can include the step of measuring the electric field at a number of points within a uniform medium. The phase center calibration can utilize a least squares approach, in another aspect, to determine where the phase center must have been in order to generate the measured electric field distribution.

In still another aspect, the step of measuring the electric field includes irradiating the target with microwave energy from a first plurality of transmitting antennas that surround a first portion of the target, the microwave energy having a single operating frequency, and receiving the microwave energy at a second plurality of receive antennas for each of the transmitting antennas. Preferably, the antennas are arranged substantially within the same plane about the target.

In still another aspect, the step of measuring the electric field includes irradiating the target with microwave energy at a single frequency from one antenna within an array of antennas configured around the target region; and receiving the microwave energy at a subset of the array of antennas. The antennas in the subset are situated, generally, on the opposite side of the target relative to the irradiating antenna. Preferably, all of the antennas are arranged substantially within the same plane about the target.

In another aspect, the step of computing the electric field includes the step of computing, through simulation, the electrical field on the fine mesh at a number of nodes corresponding to the boundaries of a plurality of finite elements. The number of nodes on the fine mesh is preferably set such that the average distance between each node is less than about (a) $1/10$th of a wavelength and (b) $1/7$th of an exponential decay within the region being discretized by the finite elements.

In still another aspect, the step of estimating electric property distributions includes estimating the distributions based upon a homogeneous distribution with values identical to a medium surrounding the target.

In another aspect, the step of computing an electric field includes the step of computing a two-dimensional field distribution utilizing hybrid element techniques. In this technique, the electric fields are determined by a finite element discretization of the target while utilizing the boundary element method to represent the surrounding homogeneous region. The step of discretizing the target with a finite element mesh (i.e., the "fine mesh") can include minimizing the number of nodes on the fine mesh so as to provide preselected electric property accuracy without excessive computing beyond that required to achieve the accuracy.

In another aspect, the step of computing an electric field includes computing one of: a two-dimensional transverse magnetic electromagnetic propagation mode, a two-dimensional transverse electric electromagnetic propagation mode, and a three-dimensional electromagnetic propagation mode.

In still another aspect, the step of estimating electric property distributions includes estimating the distributions on triangular mesh nodes corresponding to the coarse mesh discretization.

In yet another aspect, the step of computing an electric field includes computing the field on triangular mesh elements corresponding to the fine mesh discretization. The step of computing an electric field can also include computing the field on triangular mesh elements corresponding to the fine mesh discretization, and estimating electric property distributions on triangular mesh elements corresponding to the coarse mesh discretization such that a unit number of triangular mesh elements of the fine mesh fit within one triangular mesh element of the coarse mesh.

In accord with the invention, it is sometimes useful to include the step of utilizing parallel processing to process information for computing electric fields at a plurality of measurement sites for each of a plurality of transmitting antennas.

Similarly, the step of calculating the Jacobian matrix, in accord with another aspect, can include utilizing parallel processing to calculate sensitivities for electric field values at fine mesh nodes with respect to perturbing the electric property distribution at each of the coarse mesh nodes.

Note that "electric field" means a continuous distribution representing the electromagnetic field. Electric field values, on the other hand, refer to the value of the electric field at selected points, e.g., on the fine mesh.

In still another aspect, the method includes the step of adaptively modifying the coarse mesh so as to increase a density of nodes on the coarse mesh corresponding to sections of the target region with the greatest variation in $\epsilon_r$ and $\sigma$.

In one aspect, the invention uses a dual mesh scheme to reduce the number of points where $\epsilon_r$ and $\sigma$ are calculated within a region of interest. That is, a first, fine mesh is uniformly dense and is used for calculating the electric fields over the region; while a second, coarse mesh is non-uniform and less dense and is used for representing the $\kappa^2$ distribution within the region. Note that $\kappa^2$ is the complex wavenumber, squared, and includes both $\epsilon_r$ and $\sigma$ (i.e., $\kappa^2 = \omega^2 \mu \epsilon_0 \epsilon_r + j\omega\mu\sigma$, where $\epsilon_0$ is the dielectric constant of air, $\epsilon_r$ is the relative dielectric constant, and $\mu$ is the magnetic permeability of free space). The number of nodes on the coarse mesh is less than or equal to the number of individual pieces of measurement data. The dual mesh scheme thus utilizes a practical amount of measurement data and the calculation of the $\kappa^2$ distribution is performed without compromise to the accuracy of the forward solution.

In another aspect, the invention provides a calibration routine to convert 3-D measured data to a 2-D format. Such a routine is utilized because microwave antennas radiate into 3-D space; yet the reconstruction algorithm of the invention utilizes only 2-D radiation characteristics. This is important because of the nature of antennas: in 3-D, the free space loss factor (FSLF) goes as $1/R^2$ from the phase center of the antenna; while in 2-D the FSLF goes as $1/R$ (R equals the distance from the phase center to the receiver). The invention thus subtracts the data's dependency on $1/R^2$ and re-incorporates the $1/R$ factor. Specifically, the calibration routine calculates the phase center of each antenna and then modifies the amplitude relative to the $1/R^2$ and $1/R$ dependencies. The phase center is calculated by measuring the electric fields at a number of points within the uniform medium. A least squares procedure then determines where the phase center must have been to give such a field distribution.

In yet another aspect, the invention utilizes a modified hybrid element method to calculate 2-D electric fields at the measurement sites. This method is beneficial, in part, because it does not utilize approximate boundary conditions in its solution, such as when the finite element method is employed to model within and outside of the target region. The method uses a finite element discretization of only the target region while the surrounding medium (which is assumed to be homogeneous) is modeled by discretizing its boundary. This reduces the size of the region being discretized with finite elements, which beneficially reduces the size of the forward computational problem as performed at each iteration. In the prior art, the hybrid element method was used in computing the electric fields based on a $(\epsilon_r,\sigma)$ distribution on a fine finite element (FE) mesh. According to the invention, the electrical property distribution is represented on a coarse mesh; but the electric fields are computed on the fine FE mesh (e.g., the "dual mesh scheme"). Finally, the invention utilizes the hybrid element method as part of an iterative reconstruction algorithm, and not just in the context of the forward solution.

In yet another aspect, the invention constructs the Jacobian matrix as part of an iterative reconstruction algorithm (based, in part, on Newton-Raphson techniques known to those skilled in the art) to update the electrical property estimates during the non-linear iterations. The Jacobian matrix construction is intimately related to the formulation of the forward solution. Accordingly, in accord with the invention, the Jacobian matrix is calculated by determining the forward solution, via the hybrid element method, and by implementing the dual mesh scheme to compute the electric field variations at the measurement sites in response to variations of the electric properties on the coarse mesh.

In still another aspect, the invention provides an illumination chamber composed of lossy materials within the frequency range of about 300 Mhz to 1100 Mhz. In one aspect, the illumination chamber has a solid exterior, e.g., in a cylindrical shape so as to surround the target, and a liquefied interior (the target is disposed within the liquefied interior). The solid exterior is constructed of material that is substantially homogeneous as to $\epsilon_r$ and $\sigma$ so as to facilitate the calculation and measurement of the electric fields. More particularly, the homogeneous region surrounding the target is assumed to extend to infinity. This assumption is realized by suspending the target within the liquefied interior, e.g., a saline solution, and by making the chamber lossy such that any signal which travels to the outer edge of the chamber solid, and back, is attenuated such that it will not interfere with the measurement of the desired signal. In this solid/liquid chamber configuration, the antennas are imbedded in the solid either by machining holes within the solid or by curing the solid with the antennas in place.

In another aspect, the antennas are suspended within a saline bath, allowing the materials in the homogeneous surrounding medium to be exactly the same as the medium within which the target objects are suspended. In particular, in this aspect, transmitting and receiving antennas are suspended within the liquid to surround the target disposed therein. An arbitrarily-shaped fine mesh covering the target region is discretized by finite element methods; and electric property distributions are determined through a coarse mesh discretization of the region.

In accord with yet another aspect, one illumination chamber of the invention includes a shell that houses a lossy material, e.g., saline. As above, this shell also has substantially uniform electrical properties; however, its interior can be substantially identical to the target region, where the various objects are suspended for imaging.

The invention can be used over a broad frequency range, such as from about 300 Mhz to 1100 Mhz. This region is sometimes denoted herein as "microwave," even though it extends into the classically-defined radiofrequency range, because the effective wavelength of the energy within the target, typically having a dielectric constant of about 75–80, is reduced by about $1/\epsilon^{1/2}$. By way of example, a 300 Mhz wave has a free-space wavelength of about one meter; while the same wave has a wavelength of about ⅛th of a meter within a material that has a dielectric of about eighty.

In another aspect, a data acquisition system is used to obtain coherent amplitude and phase information from the microwave signals. The algorithm provides a large degree of flexibility in the selection of antennas, antenna configuration, and the background medium.

Microwave imaging systems of the invention provide several advantages. First, it provides a method of determining the 2-D electrical property distributions of non-uniform targets, which is relevant to the measure of human tissue due to the large contrast range of electrical properties. By way of example, bone and fat typically have an $\epsilon_r$ of about 5.0–6.0 at 500 MHz; while the dielectric constant of an aqueous-based tissue (e.g., liver, kidneys, and muscle) is more on the order of 50 to 70. Other modalities such as x-rays typically yield contrasts below 2:1 for a wide range of human tissue.

The large contrast provided by the invention can be exploited within several applications, such as: 1) breast cancer detection where the typical breast tissue has an $\epsilon_r$ of about 5.0 while a malignant breast tumor has an $\epsilon_r$ of about 75; 2) the measurement of air and water content within tissue, because air has a dielectric constant of 1.0 and water an $\epsilon_r$ close to 75.

In addition to the imaging of electrical properties, i.e., $\epsilon_r$, the invention can also produce temperature distributions of tissue by exploiting the substantial variation of tissue conductivity, $\sigma$, with temperature. By taking a baseline image prior to heating, and then by subtracting that image from subsequent images during heating, a temperature distribution can be derived. This has particular application in the area of hyperthermia, which applies heat primarily to a malignant region up to therapeutic temperatures. By way of contrast, magnetic resonance imaging ("MRI") is the current and primary technique of non-invasively monitoring tissue temperature, even though MRI machinery is expensive, difficult to use in conjunction with heating devices, and is only accurate to within a few degrees Celsius.

In certain preferred aspects, the invention utilizes one or more of the following:

(1) a 2-D total field inversion algorithm with an iterative approach (2) a modified hybrid element method to compute electric fields (3) a dual mesh scheme to reduce the number of points where $\epsilon_r$ and $\sigma$ are calculated, which in turn reduces the required amount of measurement data (4) a calibration procedure to transform 3-D measurement data to a 2-D configuration for image reconstruction By combining (1)–(4), the invention acquires 2-D images that quantifies (a) a target's size and shape, as well as (b) material $\epsilon_r$ and $\sigma$. This result is achieved even for biological systems with high contrast, such as 16:1, for both the dielectric constant and conductivity.

In one aspect of the invention, the modified hybrid element method is replaced by a hybrid scheme such as the boundary element method for the homogeneous surrounding medium and the finite difference method, or the moment method, for the inhomogeneous target region.

In still other aspects, the invention preferably operates in the 2-D TM ("transverse magnetic") electromagnetic propagation mode. However, in other aspects, the invention is utilized in the 2-D TE ("transverse electric") propagation mode or in a 3-D mode.

In general, there are three key features in a microwave imaging system of the invention: 1) the electric fields are measured accurately and reliably: 2) the numerical algorithms for calculating the electric fields based on the electrical property distribution and electromagnetic excitation are accurate; and 3) data reduction techniques reduce the amount of required measured data without compromising image quality. Feature (3) is important as it can seriously impact the complexity and cost of the system hardware.

The invention thus provides a 2-D microwave imaging system for reconstructing electrical properties in matter such as human tissue. The system has application, for example, in monitoring temperature changes of tissue during hyperthermic therapy, e.g., cancer treatment, because of the strong temperature dependence of the tissue's electrical conductivity. The system also provides higher contrast range (approximately 20:1) in soft tissue properties as compared to the conventional modalities such as computerized tomography ("CT"), thereby increasing the understanding of tissue functionality. The invention also has use in industrial applications such as in the monitoring of two-phase flow in pipes.

These and other aspects and advantages of the invention are evident in the description which follows and in the accompanying drawings.

BRIEF DESCRIPTION OF THE DRAWINGS

A more complete understanding of the invention may be obtained by reference to the drawings, in which.

DETAILED DESCRIPTION OF THE INVENTION

Figure 1:
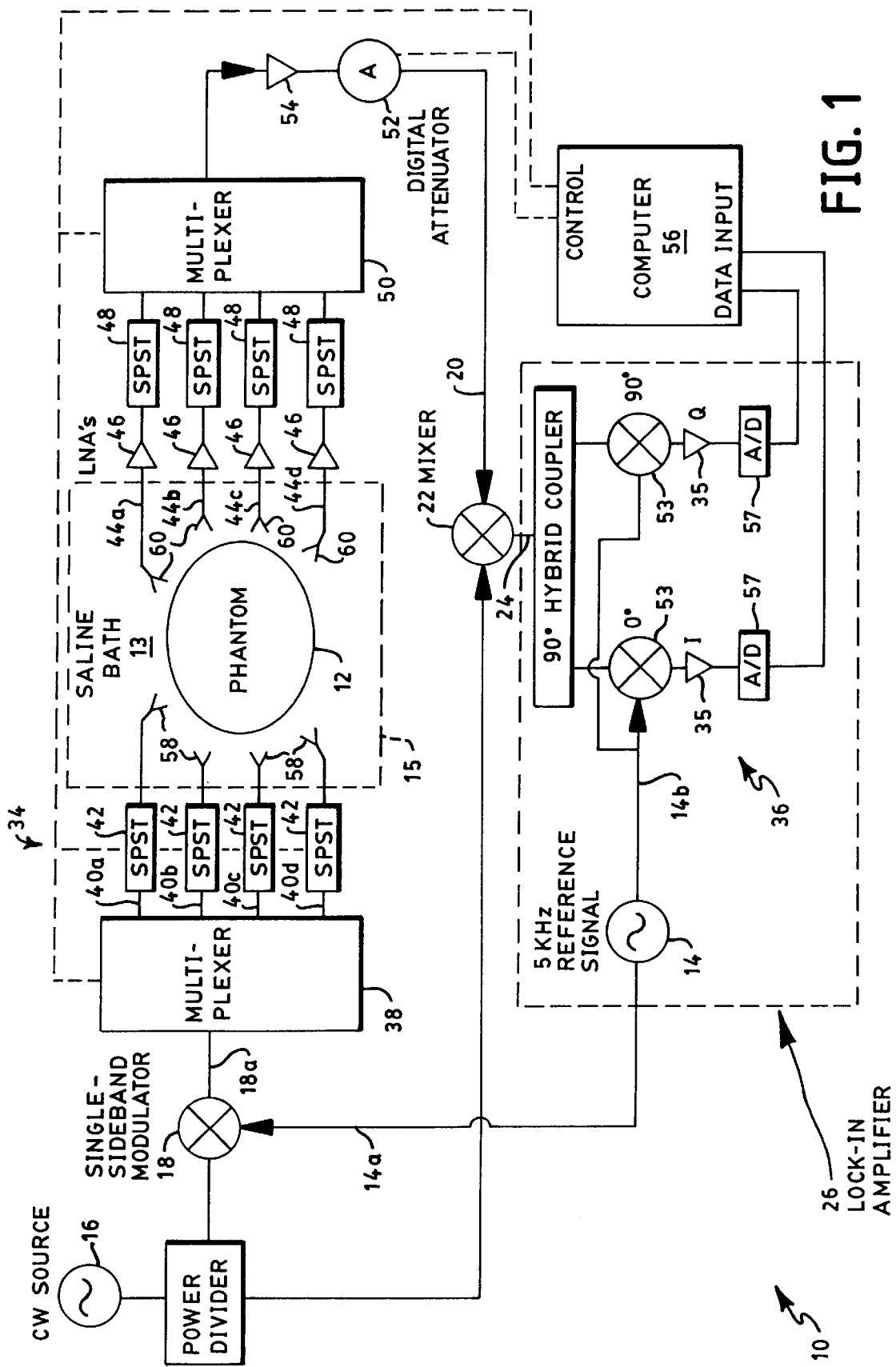
FIG. 1 illustrates a schematic diagram of a 2-D microwave imaging system constructed according to the invention.

FIG. 1 illustrates one system 10 constructed according to the invention and which was used experimentally to reconstruct both resistive and reactive components of the electrical property profile of a target medium 12 ("phantom"). The system 10 is coherent and retains both phase and amplitude information of received signals. Variations due to differences in the transmit/receive channels are calibrated out by data processing. After data acquisition, the data is modified because the antennas 58 of system 10 irradiate the phantom 12 in three dimensions, while the image reconstruction algorithm of the invention is two-dimensional. Once the measurements are processed, the reconstruction algorithm utilizes the modified data to obtain profiles of the electrical properties.

In the preferred embodiment of the invention, the reconstruction algorithm utilizes Newton's iterative method, known to those skilled in the art, see, e.g., Paulsen et al., *Temperature Field Estimation Using Electrical Impedance Profiling Methods: I. Reconstruction Algorithm and Simulated Results*, International Journal of Hyperthermia, vol 10, pp. 209–228 (1991), and a hybrid of finite element and boundary element methods to calculate the electric fields at each iteration. See, Lynch et al., *Finite Element Solution of Maxwell's Equations for Hyperthermic Treatment Planning*, Journal of Computational Physics, vol 58(2), pp.246–9 (1985); Paulsen et al., *Memory and Operations Count Scaling for Coupled Finite Element and Boundary-Element Systems of Equations*, International Journal for Numerical Methods in Engineering, vol 33, pp. 1259–1304 (1992); and Meaney et al., *Two-dimensional Hybrid Element Image Reconstruction for TM Illumination*, IEEE Transactions on Antennas and Propagation, vol. 43, pp.239–47 (1995), each of which is incorporated herein by reference.

The reconstruction process according to the invention also incorporates a "dual mesh" scheme, which particularly impacts two areas of the hybrid element method: (1) the forward solution at each iteration for the electric fields, which must account for the more coarsely defined electrical property distribution, and (2) the calculation of the Jacobian matrix, which is used to update the electrical property estimates during the non-linear iterative process. The reconstruction process, including the dual mesh scheme, are described in greater detail below.

System 10 utilizes four transmit channels and four receive channels to cover the broad frequency range of 300 MHz to 1100 MHz. This microwave span permits an optimal frequency selection based upon trade-offs of resolution size and signal penetration depth; and also provides multi-spectral excitations which can help discriminate between blood flow and temperature-related electrical property changes. The system 10 utilizes low cost, well-characterized microwave components to reduce system integration problems. Its modularity also allows for testing of multiple antennas in various positions so as to optimize the use of the space around the target region.

System 10 extracts both the real ("Q") and imaginary ("I") parts of the electrical properties of the phantom 12. A reference continuous wave ("CW") signal 16 is modulated with an intermediate frequency ("IF") signal 14 using a single-sideband, carrier-suppressed up-converter 18. The received modulated signal 20 is then compared with the original reference CW signal 16 using a single mixer 22; and the resulting IF signal 24 is fed into a lock-in amplifier 26 (e.g., EG&G Princeton Applied Research, Princeton, N.J.), which extracts the I & Q components and which also performs A/D conversions.

The arrangement of FIG. 1 is preferable because I & Q discrimination can be accomplished in the kHz frequency range which is more accurate and less expensive than measuring the phase and amplitude directly from the microwave signal 16.

Figure 2:
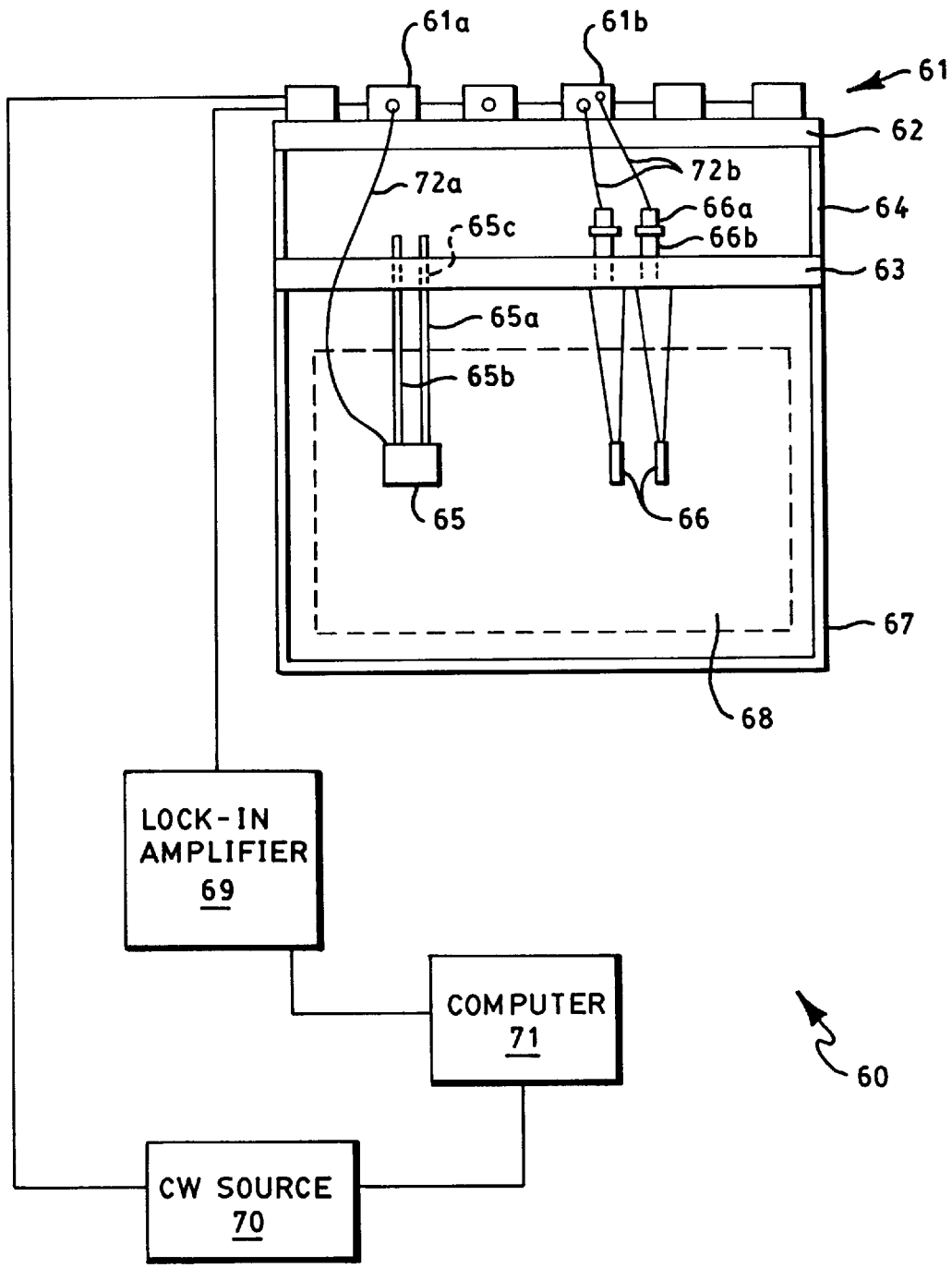
FIG. 2 shows a schematic side view of a microwave imaging system constructed according to the invention, similar to the system of FIG. 1, whereby microwave components and antennas are suspended relative to an experimental bath of saline solution.

System 10 is constructed modularly such that all microwave components reside on a single microwave plate and such that the antennas are suspended from a single antenna plate. The two plates are spaced from each other with appropriate spacers and relative to an experimental imaging tank. FIG. 2 illustrates one such arrangement 60, showing a schematic side view of a system such as system 10 of FIG. 1. As noted, the microwave components 61 are arranged on a microwave plate 62, which is spaced above the antenna plate 63 by spacers 64. Note that, for illustration purposes, the components 61 are arbitrarily represented by six elements. The transmitter antennas, shown for illustrative purposes as a single waveguide antenna 65, are suspended through the antenna plate and connect to a transmitting microwave component 61a. The receiving antennas, shown for illustrative purposes as two monopole antennas 66, connect to the receive microwave components 61b via connection 66a above the plate 63. Both transmit and receive antennas 65,66 are suspended into the tank 67 which includes a saline solution 68. The components 61 also connect to a lock-in amplifier 69, a CW source 70, and a computer 71, such as described in connection with elements 26, 16 and 56, respectively, of FIG. 1.

The arrangement of FIG. 2 makes efficient use of available space and shortens the distance of the transmission lines 72a, 72b between the microwave components and antennas, thereby reducing potential phase shifts due to mechanical stressing during measurements. It also allows ease of assembly or disassembly of the systems 10, 60 in the event that components require alteration or servicing.

In the transmitter and receiver configuration of FIG. 1, the reference CW signal 14 is divided into two parts, one part 14a going to the transmitter 34, and the other part 14b going to the receiver 36 for later comparison. The signal 14b is preferably amplified and attenuated (not illustrated) prior to modulation to increase the isolation between the transmitter 34 and receiver 36. The transmitter signal 14A is then modulated by a single-sideband, carrier-suppressed modulator 18, e.g., Merrimac IGM-9B Series, I and Q Phase Demodulator (Merrimac, West Caldwell, N.J.), which yields an output signal of −16 dBm with the sideband and carrier suppressed to −25 dBc or better over the frequency range 300 MHz to 1100 MHz.

As known to those skilled in the art, greater sideband and carrier suppressions are available over narrow bandwidths. However, the design of FIG. 1 was chosen because of its wide bandwidth to facilitate: (a) an evaluation of the frequency performance of system 10, and (b) the selection of an optimal operating frequency and with possible multi-spectral excitations for in vivo uses.

The modulated signal 18a is fed into a power amplifier (not shown) and then a multiplexer (SP4T switch) 38, e.g., M/A-COM SW-255 (M/A-COM Microelectronics Division Lowell, Mass.), which selects the transmitting channel 40a–d. The multiplexer 38 has isolation between about 50 dB and 60 dB across the band to reduce or eliminate leakage signals caused by the antenna configuration and the high attenuation of the saline bath 13. A M/A-COM SW-215 switch 42 or equivalent is incorporated at the four outputs 40a–d of the multiplexer in order to achieve a linear dynamic range goal of greater than about 115 dB.

Each receiver channel 44a–d includes a cascade of (M/A-COM) broadband components: (1) a low noise amplifier 46, e.g., AMC-174, (2) an isolating (SPST) switch 48, e.g., M/A-COM SW-215, (3) a multiplexer 50, e.g., M/A-COM SW-255, (4) two 5-bit digital attenuators 52, e.g., AT-104 (note that only one is illustrated), (5) two amplifiers 54, e.g., AMC-184 (note that only one is illustrated), and (6) a mixer 22, e.g., MDC-149.

The linear dynamic range of system 10 is bounded at the low end by the signal-to-noise ratio of the system 10, and at the high end by the saturation of the component most likely to see power levels approaching its 1 dB compression point, which in system 10 is the mixer 22. Attenuating the signal in known increments using the digital attenuators 52 allows the mixer 22 to operate in the linear region while still maintaining accurate phase and amplitude data. The resulting IF signal 24 is fed into the lock-in amplifier 26 for I & Q discrimination by the hybrid coupler 51 and phase discriminators 53. The I, Q signals are then amplified by amplifiers 55, and, eventually, put into digital form by the A/D components 57. Control of all the switches 42, 48, attenuators 52, multiplexers 38, 50, microwave sources 16, 14, and lock-in amplifier 26 is performed by a computer 56, e.g., a Dell Dimension 486 computer.

Figure 3:
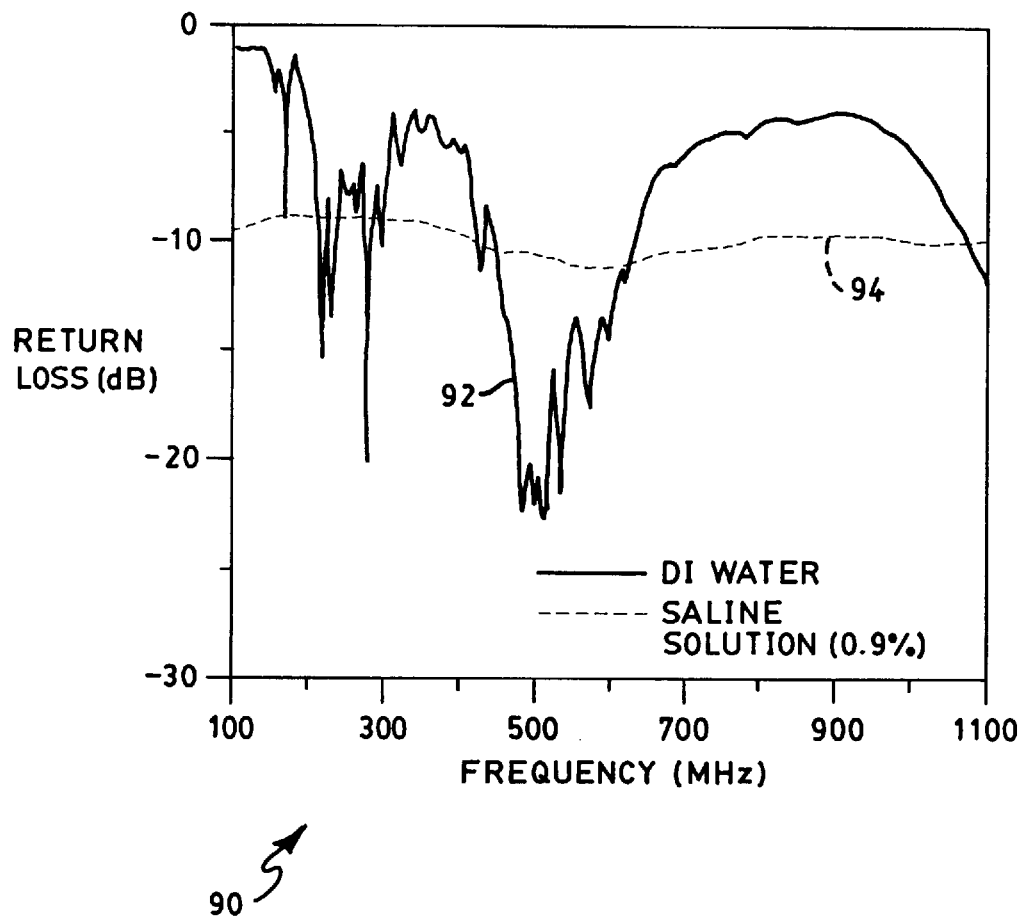
FIG. 3 illustrates characteristic impedances for a monopole antenna within deionized water and saline, in accord with the invention.

Water-filled waveguide apertures, known to those skilled in the art and such as illustrated as antenna 65 of FIG. 2, were used as the transmit antennas 58. They yield a certain degree of directivity without significant increase in size, which is important in reducing the signal loss from the transmitter to receiver in a lossy medium. For the receive antennas 66, monopoles were chosen because they closely emulate a point electric field detector in a 2-D plane. They were constructed by exposing a quarter wavelength (in the medium) of the center conductor of a semi-rigid coaxial cable 72b, FIG. 2. In a low loss medium, such as air or deionized ("DI") water, these monopole antennas 60 behave poorly and excite currents along the outside of the coaxial cable 72b. Methods of improving the performance of the antennas 60 generally take two forms: incorporating a balun in an attempt to properly terminate unwanted currents, and (2) use of an absorptive material such as a ferrite ring around the outside of the cable to attenuate the currents. Both of these generally have limited bandwidths. The approach utilized in the system of FIG. 1 capitalizes on the high attenuation of the surrounding saline solution 13. FIG. 3, for example, shows a graph 90 with the characteristic impedances of the monopole antenna in DI water and in 0.9% saline solution. The DI water trace 92 is quite uneven, displaying characteristics which are generally attributable to the lack of any sort of balun. The trace 94 for the saline solution 13, on the other hand, is dramatically different: it is well-behaved over a broad bandwidth, with a nominal return loss of 9 dB for the frequency range of 300 MHz to 1100 Mhz.

Similar advantages were also exploited to minimize mutual coupling of the various antennas 58, 60. When the return loss of an antenna is measured in the presence of another receiver antenna (e.g., via separations of about 2.8 cm minimum), there is no detectable change. This is due primarily to the high attenuation of a radiated signal during its round trip from one antenna to another and back again. This source/detector arrangement is fairly close to the TM electromagnetic mode, where the electric field is predominantly in the vertical direction for semi-infinitely long cylinders; and hence is suitable for use in 2-D image reconstruction.

During data collection, the positions of the various antennas 58, 60 are known accurately in order to correlate to the numerical model. If a position is in error by 1 cm, a 55° phase shift can occur at 500 MHz. It is also relatively important that the antenna alignment fixtures are not cumbersome so as to perturb the electric field patterns.

As shown in FIG. 2, the system 60 suspends its transmit antennas 65 from the antenna plate 63 situated above the experimental tank 67. Plexiglass rods 65a, 65b are fixed at known locations on top of the waveguides and are suspended through holes 65c in the antenna plate 63. A tapered metal sleeve 66b is soldered to the coaxial cable 72b of the monopole antenna 60, for stability, and is also mounted to the antenna plate 63. All mounting holes 65c in the antenna plate were drilled by a CNC milling machine to ensure antenna position accuracy.

The system 10 is described for illustrative purposes and those skilled in the art should appreciate that a more complex system is envisioned, with additional or moveable transmit/receive channels, so as to achieve enhanced microwave imaging characteristics. More particularly, four transmit channels and four receive channels are not enough to get a full data set required for practical imagery. However, in accord with the invention, antennas can be moved to various positions to acquire the full data set, such as with a transmitter in eight different locations, and with receive data being measured at eighteen different locations for each transmitter.

In FIG. 1, the fine mesh is defined with arbitrary shape within the saline bath 13 and preferably near to the antennas 58, 60. As shown, the phantom 12 can effectively define the region discretized by the fine mesh; and a plurality of objects with varying electrical properties $\epsilon_r$, $\sigma$ can be isolated within the phantom 12 relative to their electrical property distributions on the coarse mesh, which is also thus bounded in area by the phantom 12.

Figure 4:
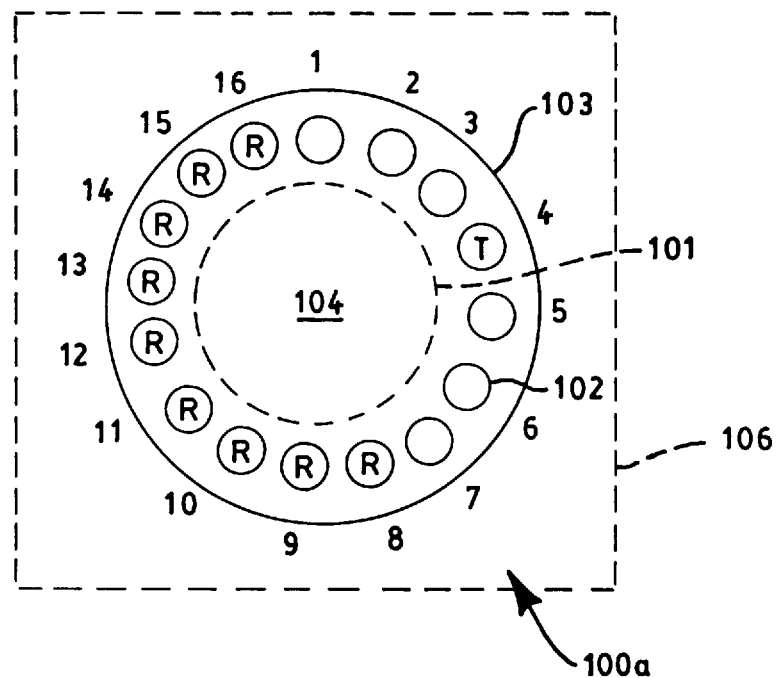
FIGS. 4 and 4A illustrate a concentric arrangement of monopole antenna banks constructed according to the invention, and operating in two operational configurations of transmit and receive antennas.
Figure 4A:
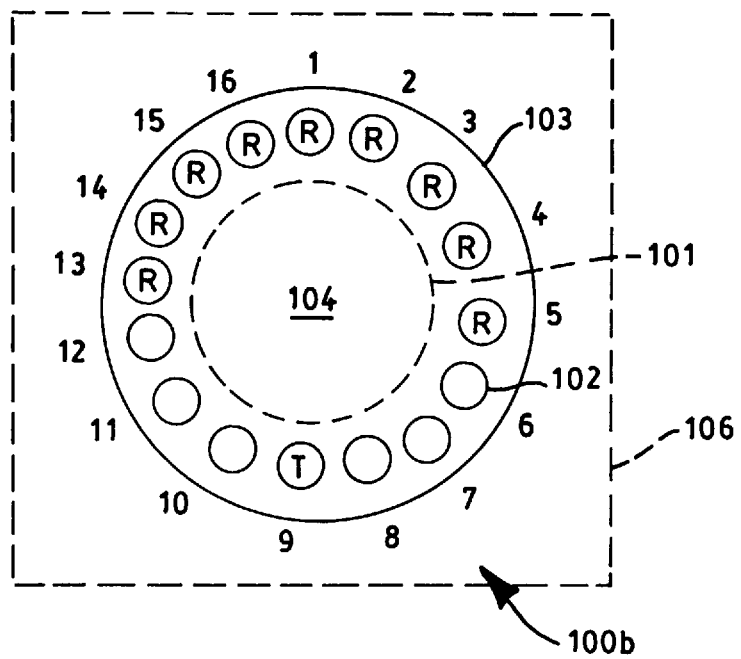

Those skilled in the art should appreciate that other modifications of FIG. 1 can be made within the scope of the invention. By way of example, the waveguide antennas 65 of FIG. 2 can be replaced with monopole antennas, such as antennas 66, and additional antennas can be used. FIGS. 4 and 4A show one cavity configuration 100 according to the invention (specifically, FIG. 4 shows the cavity in a first operational condition 100a; while FIG. 4A shows the cavity in a second operational condition 100b). Instead of four transmit and receive antennas as in FIG. 1, FIGS. 4 and 4A have sixteen monopole antennas 102 that can function as either active, transmit antennas or as receive antennas denoted with a "T" and "R," respectively. The antennas 102 are arranged into a circle about the sample region 104 (for illustrative purposes, the positions of each of the antennas 102 are numbered with a unique number between "1" and "16"). Each antenna 102 is switched through a switching matrix 106 so as to operate as a transmitting antenna "T" or as a receiving antenna "R." When a single "T" antenna 102 is transmitting, nine receiving "R" antennas 102 are selected so as to form an arc across the target region 104 from the transmitting "T" antenna 102. Thus, for example, when antenna number "4" is operating as a transmitting "T" antenna, the opposite nine receiving "R" antennas occupy positions "8" through "16," such as shown in the operational configuration 100a of FIG. 4. In the second operational configuration 100b of FIG. 4A, the transmitting "T" antenna is illustratively shown in position "9" while the receiving "R" antennas occupy positions "13" through "5." This process is repeated for all sixteen possible antennas 102 operating as a transmitting "T" antenna, providing one hundred and forty-four pieces of measurement data (i.e., sixteen transmitters times nine receivers "R" per transmitting antenna "T").

Note in FIGS. 4 and 4A that the boundary between the target region 104 and the solid outer core 103 which houses the antennas 102 is denoted by a dotted circle 101. The boundary 101, in this illustrated cavity configuration, also forms the boundary within which the fine and coarse meshes are determined. That is, the electric field of target 104 is determined by a fine mesh discretization of finite elements within the target area 104; and the electric properties $\epsilon_r$ and $\sigma$ are determined within the same region 104 by a coarse mesh discretization as described herein. The core 103 is modeled with homogeneous electrical properties so that an electric field can be calculated at several points within the core 103, e.g., at each antenna location "1" through "16."

The system 10 of FIG. 1 provides microwave-based imaging for applications such as hyperthemia treatment monitoring and assessment. As illustrated, a four transmit channel and four receive channel hardware device and concomitant image reconstruction algorithm, described in more detail below, are used. The hardware of FIG. 1 measures electric fields (i.e. amplitude and phase) at various locations in a phantom tank 15 with heterodyning principles. The receiver 36 has a dynamic range of better than 115 dB in order to image biological tissue with high electrical permittivity and high conductivity within a highly lossy saline bath 13.

The microwave measurement system 10 also includes a calibration procedure, described in more detail below, to convert data from radiation generated into 3-D space into a 2-D representation for the reconstruction algorithm. Specifically, the calibration procedure compares the data from the forward solution for the electrical fields in a known homogeneous medium with the measured data from the actual medium and modifies the measurement data accordingly. The reconstruction algorithm is then applied to the calibrated measurement data for several phantoms to quantitatively generate an image of objects that are about ½λ in size, or larger (this quantitative image includes object location, size and electrical properties for both resistive and reactive components). Objects that are smaller than about ½λ have qualitatively correct images, though without detail such as electrical properties.

Reconstruction Algorithm

The reconstruction algorithm of the invention utilizes an iterative method, such as Newton's iterative scheme, to obtain a measure of the electrical properties, $\epsilon_r$ and $\sigma$, within a target region. Briefly, the algorithm includes the following steps:

(1) Guess of the initial property distribution, $\{\kappa_0^2\}$;
(2) Calculate the electric field at measurement sites based on $\{\kappa_i^2\}$;
(3) Compute updates to the electrical property distribution, $\{\Delta\kappa^2\}$;
(4) Use updates to calculate the new electrical properly distribution, $\{\kappa_i^2\}$;
(5) Re-compute the electric field at measurement sites based on the new electrical property distribution, $\{\kappa_i^2\}$; and
(6) Compare measured electric field values with the calculated values, where k is the complex wavenumber, including an embedded dielectric constant and conductivity.

In the iterative approach, steps (3)–(6) are repeated until the fluctuations of the RMS electric field error reaches a selected stopping criterion (e.g., when the image or data reaches a steady-state behavior relative to further iterations, or when the image is acceptably defined). In order to process these steps, the invention utilizes modified hybrid element methods, such as described in Appendix A hereto, and a dual mesh scheme, such as described in Appendix B hereto. In particular, the modified hybrid element method is used to calculate the electric fields of step (2) above so as to provide high accuracy with appropriate sampling of the target region (e.g., the phantom 12 of FIG. 1). Certain hybrid element techniques have been in existence in the prior art since 1985. See, e.g., Lynch et al., *Finite Element Solution of Maxwell's Equations for Hyperthermic Treatment Planning*, Journal of Computational Physics, vol 58(2), pp. 246–9 (1985). However, those techniques were shown to be most efficient only when solving for the electric fields in a forward solution based upon an electric property distribution on its finite mesh. See, Paulsen et al., *Memory and Operations Count Scaling for Coupled Finite Element and Boundary-Element Systems of Equations*, International Journal for Numerical Methods in Engineering, vol 33, pp. 1259–1304 (1992). However, this is not true when used in the context of the reconstruction algorithm according to the invention, where the modified hybrid element method is used to compute the electric fields based on an electrical property distribution defined over a coarse mesh which overlaps the fine mesh used for the electric field computation. Further, and unlike the prior art, the modified hybrid element method of the invention also incorporates the computation of the Jacobian matrix, as described in Appendix A, which is used in solving for the electrical property updates in step (3) above.

More particularly, the dual mesh scheme, set forth in Appendix B hereto, is used to reconstruct the electric field without calculating $\epsilon_r$ and $\sigma$ at each point in the fine mesh, which would be very difficult because the high density and sampling of the mesh as governed by the equations $\mathrm{Re}(\kappa^2\Delta x^2)<0.4$ and $\mathrm{Im}(\kappa^2\Delta x^2)<0.02$ (note that these criteria correspond to the sampling of ten nodes per wavelength and seven nodes per exponential decay, as discussed above). If the classical hybrid element techniques of the prior art were used, it would increase the computational time unreasonably as a cubic function with respect to the number of electrical property values ($\epsilon_r$, $\sigma$) being reconstructed; and it would simultaneously increase the amount of measured data, linearly, with respect to the number of electrical property values. The dual mesh scheme of the invention thus enables a coarse sampling of the electrical property distribution (with the $\kappa^2$ mesh) because material properties do not generally vary as dramatically as the electric fields. This reduces the reconstruction problem by an amount corresponding to the size and the amount of measured data acquired.

Microwave imaging systems of the invention extract phase and amplitude information of the transmitted and subsequently received microwave signal. Specifically, in a preferred embodiment, the invention detects the phase and amplitude using a broadband, low-noise, single-side band heterodyning transmit/receiver system such as illustrated in FIGS. 1 and 2. Such a system transmits and receives at the desired frequency range, and then converts to a 5 kHz reference for the I & Q discrimination (where it is much more accurate and less expensive) while retaining phase and amplitude information. In accord with the invention, the system further calibrates the transmit and receive channels so as to remove residual differences, and maps the three-dimensional ("3-D") measured data into two dimensions ("2-D") via the calibration procedure. Specifically, the invention extracts the 3-D free space loss factor ("FSLF") from the measured data by first determining the radiator's phase center through a least squares approach and then reintroduces the 2-D FSLF.

The system of the invention preferably utilizes quarter wave monopole antennas to acquire practical microwave image data, such as described in Appendices A, B hereto. In one simplified embodiment, such as described in connection with FIG. 2, these ¼λ antennas can be formed by exposing the center conductor of a coaxial cable for a quarter wavelength distance to generate an isotropic radiation pattern in the 2-D plane. However, such antennas also have fairly poor impedance characteristics; and create hard-to-terminate currents outside of the cable. Accordingly, in accord with the invention, these ¼λ monopole antennas are placed in a highly lossy medium (e.g., 0.9% saline) that increases the usable bandwidth and that improves their overall characteristics.

Figure 5:
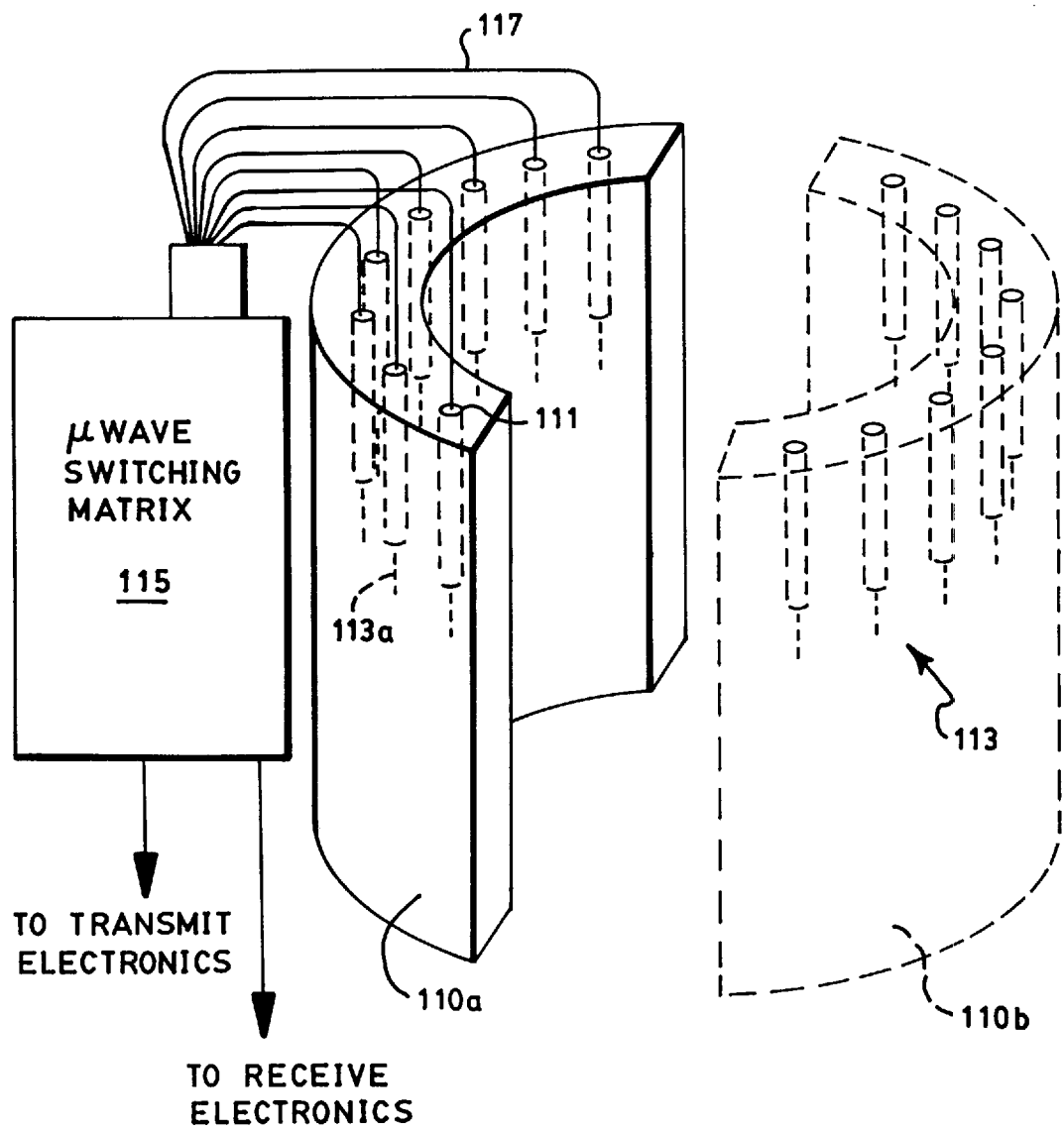
FIG. 5 shows a perspective view of a split-block illumination chamber, constructed according to the invention, for mounting monopole antennas therein.

The use of monopole antennas for transmission and for reception has other benefits. First, such antennas can be integrated within a surrounding medium made of solid material because they are easily embedded within the material, such as by drilling. Conventional antennas, on the other hand, generally form waveguides that (a) are not practically imbedded within a solid medium, and (b) encourage a water-filled target region, which would be inconvenient in clinical and industrial environments. In one embodiment of the invention, such as shown in FIG. 5, a split-block cylinder 110 is made out of polyester resin ($\epsilon_r \approx 2.5$) as the binder, a high dielectric ceramic powder ($\epsilon_r = 250$ to 300) and silver powder, providing a high dielectric constant and high conductivity to mimic the electrical properties of saline ($\epsilon_r \approx 75$ and $\sigma = 1.8$ at 500 MHz). Drill holes 111 are made for the several monopole antennas 113 disposed within the cylinder 110. Note that the cylinder 110 is made into two halves, one half 110b illustrated as a dotted outline for purposes of illustration, and one half 110a illustratively connected to supporting electronics 115 via interconnections 117.

In operation, the two halves 110a, 110b are joined (shown illustratively in FIG. 5A) to form an illumination chamber which surrounds a lossy bath such as saline so that (a) there are effectively no reflections from outside surfaces of the chamber, (b) there is reduced interaction between antennas, and (c) there is suppression of any unwanted surface waves.

FIG. 5 also illustrates the various monopole antennas can be made from coaxial cables imbedded within the core 110, where each of the cables are stripped to expose the center conductor 113a for the antenna.

Figure 5A:
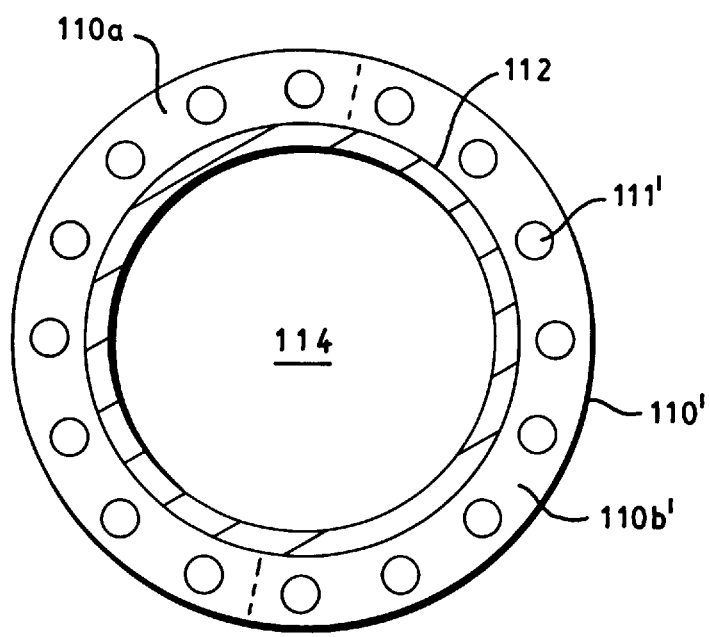
FIG. 5A shows a cross-sectional view of a chamber, such as illustrated in FIG. 5, used in an operational mode.

As shown in FIG. 5A, the split-block 110' is easily wrapped around an existing PVC pipe 112 so that the electrical properties of the cross-sectional area 114 are quantitatively imaged through transmit and receive antennas 116 disposed within the through-holes 111'. The configuration of FIG. 5A has direct application, for example, in the cross-sectional and quantitative measure of ($\epsilon_r, \sigma$) in multiphase flow in pipes.

The split-block configurations of FIGS. 5 and 5A illustrate certain advantages of the invention relative to implementing the modified hybrid element method. As discussed above, this method is beneficial, in part, because it does not utilize approximate boundary conditions in its solution. Rather, the method uses a finite element discretization of only the target region while the surrounding medium (which is assumed to be homogeneous) can be modeled simply by discretizing its boundary. In the example of FIGS. 5 and 5A, the split-block 110 is "homogeneous" and very lossy for the attenuation of any signals propagating to its extremities and reflecting back into the target region; thus providing for a very accurate calculation of electrical properties.

Figure 5B:
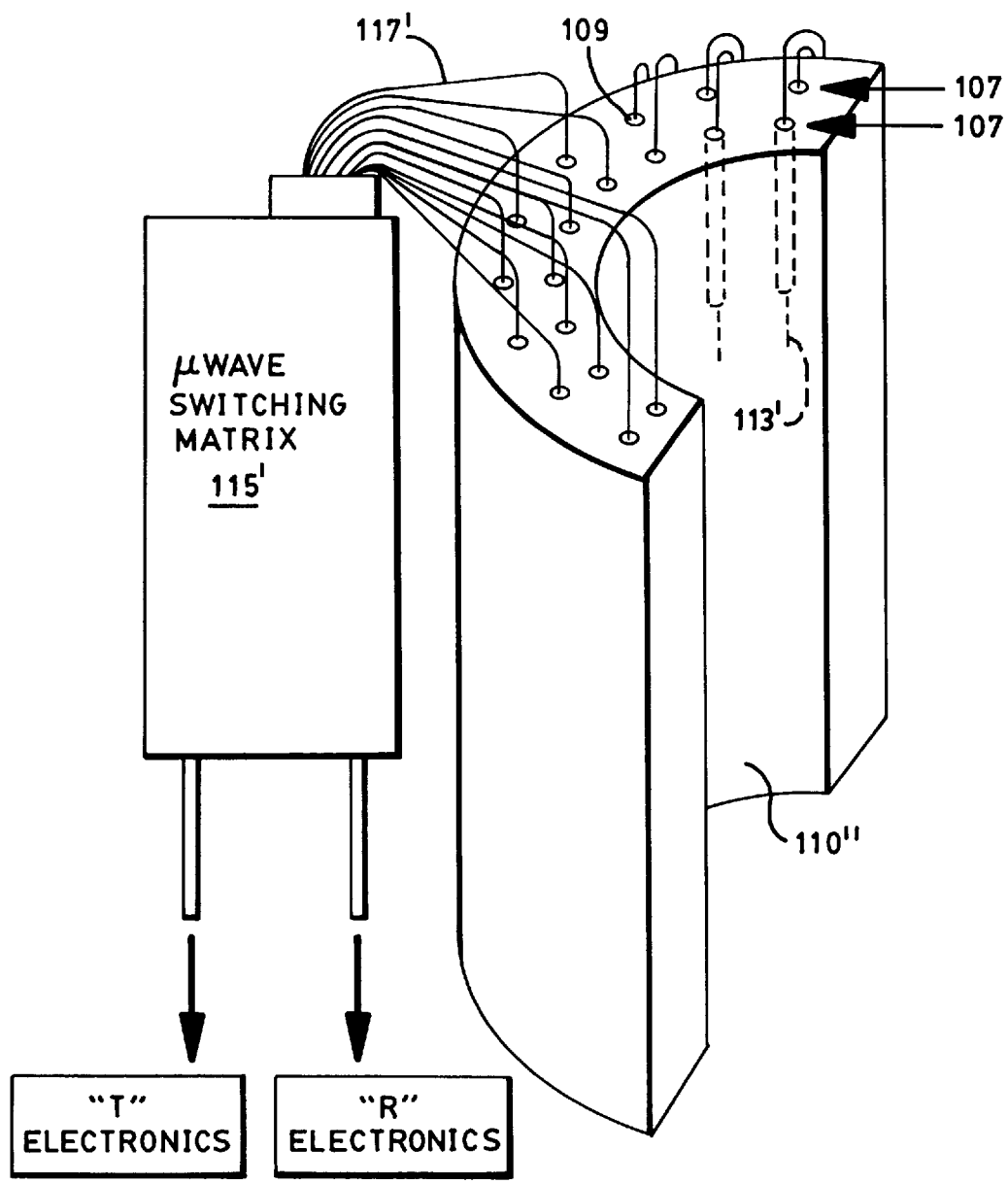
FIGS. 5B and 5C show perspective views of other split-block illumination chamber structures constructed according to the invention.

FIG. 5B illustrates yet another split-block configuration, where sixteen antennas 113', for example, are made into two arched banks 107 of eight concentric antennas 113' each (note for clarity of illustration that only two antennas 113' are illustrated as dotted outlines since they are internal to the core structure 110"; yet sixteen antenna apertures 109 are shown where the antennas 113' are imbedded within the core material 110" and where the electrical connections 117' to the antennas 113' connect to the supporting electronics 115'). The dual banks 107 can be used to increase the amount of measurement data for a given phantom since data from eighteen receive antennas are collected simultaneously as opposed to the nine receive antennas discussed above.

Figure 5C:
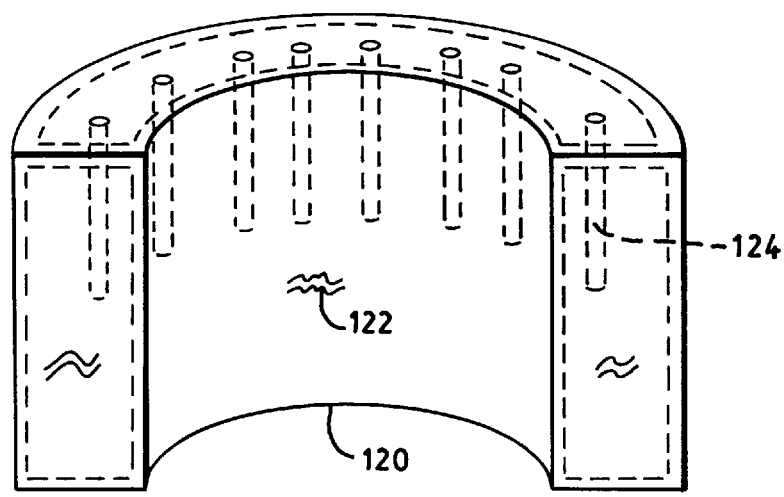

The illumination chamber or split block configurations of FIGS. 5, 5A and 5B can also be constructed with a outer rigid shell which houses a lossy material, e.g., saline. In FIG. 5C, for example, an outer shell 120 houses a saline solution 122 disposed within the shell 120. A plurality of antennas 124 are disposed within the shell and within the saline 122, thereby creating an environment within the shell 120 that is substantially equal to the environment consisting of the target objects suspended within a saline bath, such as in FIG. 1.

Figure 6:
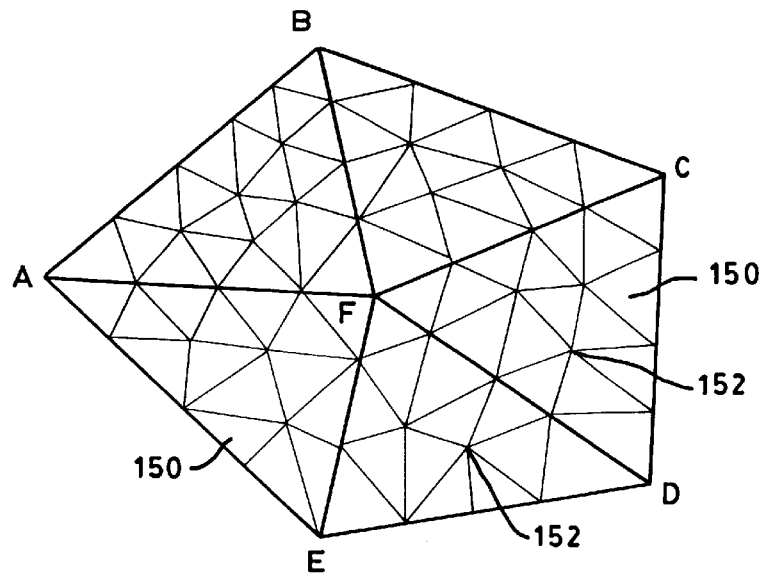
FIG. 6 illustrates dual mesh sampling on a target region, in accord with the invention.
Figure 6A:
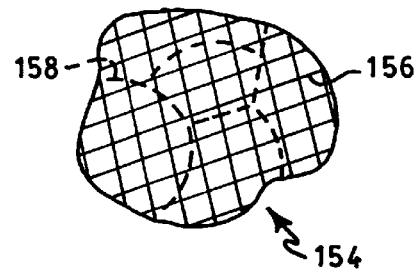
FIG. 6A illustrates another dual mesh sampling scheme on a target region, where the coarse mesh and fine mesh do not have corresponding nodes.

With reference to FIGS. 6, 6A, the dual mesh scheme of the invention can include a variety of mesh configurations. In one case, illustrated in FIG. 6, the fine and coarse meshes overlap with common triangular elements. That is, the values of the coarse mesh properties $\epsilon_r$ and $\sigma$ are bounded by nodes A, B, C, D, E, and F, forming coarse mesh values for each of the triangles AEF, EDF, DCF, CBF, and BAF. Each of the finer triangles 150 fit exactly into one of these larger coarse mesh triangles so that the nodes 152 of the fine mesh include the nodes A,B,C,D, E and F defining the coarse mesh.

FIG. 6A, on the other hand, shows a target region 154 that is discretized by a fine mesh 156, for the electric field, and a coarse mesh 158 (shown in dotted line) that defines the target 154. Note that the coarse mesh 158 and fine mesh 156 do not have overlapping nodes; although their coverages do of course overlap the target 154. Although it is computationally advantageous, note also that the dual mesh scheme need not utilize only triangular mesh elements (the mesh 158 is not triangular). Accordingly, other more complicated mesh element shapes such as quadrilaterals can be used in the invention. In addition, the invention generally applies simple linear basis functions over the mesh elements, although it is acceptable to utilize other basis functions and to utilize Gaussian quadrature integration techniques.

Certain advantages can be achieved through the utilization of parallel processing. At present, a typical iteration for the reconstruction algorithm takes about ten minutes of CPU time, with most images converging to the best image in four iterations or less. Thus, it takes roughly forty minutes per image. Parallel processing provides significant advantages when used with the invention. Note, for example, that the computation of the electric fields is done at each iteration; and that the computation of the electric fields is performed for several different boundary conditions (e.g., 16, as illustrated above in FIG. 4), with each one corresponding to the different radiators (e.g., 16, as illustrated in FIG. 4 above), while utilizing the same matrix for each calculation. Thus, for computational purposes, solving for the electric fields for all of the excitations due to the different radiators is virtually an identical process. With an expansion of the number of antennas to 32 or 64, or more, parallel processing will become even more advantageous.

Similarly, the Jacobian matrix is computationally intensive and also lends itself to parallel processing. In forming this matrix, the invention calculates the sensitivity of the electric field values at the measurement sites with respect to perturbing the $\epsilon_r$ and $\sigma$ at each node.

In particular, the following equation is solved for the electric field vector, $\overline{E}$, at each iteration:

$$[A]\{\overline{E}\}=\{\overline{b}\},$$

where $[A]$ is the forward solution matrix, and $\{\overline{b}\}$ is a vector representing the boundary condition. The derivative is then taken with respect to the electrical properties for every coarse mesh node and every radiator:

$$\left[\frac{\partial A}{\partial k_i^2}\right]\left\{\vec{E}\right\}=-[A]\left\{\frac{\partial E}{\partial k_i^2}\right\}.$$

This equation is used to solve $$\left\{\frac{\partial E}{\partial k_i^2}\right\},$$

since $[A]$, $\overline{E}$ are already known. A matrix $$\left\{\frac{\partial A}{\partial k_i^2}\right\}$$

is thus formed where its coefficients are the derivatives of the individual terms of the matrix $[A]$ used in the forward solution of the electric fields. These coefficients are computed with respect to the electrical properties, $k_i^2$, at a single node on the coarse mesh. This new mesh, in combination with the original matrix $[A]$ used in the computation of the electric fields and the current calculated values of the electric field $\overline{E}$ are used to compute the variations of the electric fields due to the variation of the electrical properties, e.g., $$\left\{\frac{\partial E}{\partial k_i^2}\right\},$$

at a single coarse mesh node, for a single radiator. The terms $$\left\{\frac{\partial E}{\partial k_i^2}\right\}$$

make up the Jacobian matrix. Thus, to build the whole Jacobian matrix, the process is repeated for all of the radiators and all of the nodes. This time-consuming process is efficiently done in parallel.

By processing the above processes in parallel, the time to recover a complete image can be reduced to about one minute, or less. Parallel processing techniques are known to those skilled in the art. Parallel processing computers, for example, are also being developed in cost-effective ways, as evidenced by the Peregrine project at Lawrence Livermore Labs in Berkeley, Calif., which consists of many high-powered PC boards configured in parallel for use in Monte Carlo simulations.

Figure 6B:
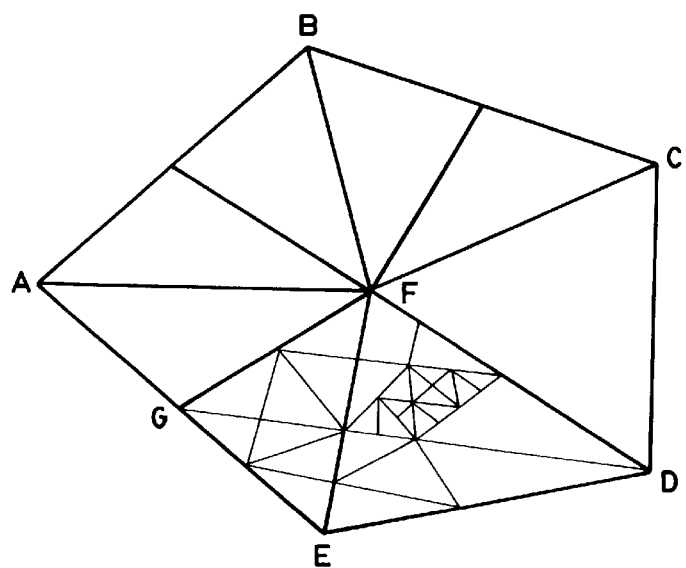
FIG. 6B illustrates adaptive coarse mesh sampling in accord with the invention.

The invention also provides for adaptive meshing. In the simple embodiments illustrated above, a single coarse mesh is used over the fine mesh in reconstructing images. The coarse mesh spatial sampling rate is basically what determines the spatial resolution of the image, provided there is an adequate signal to noise ratio. In many biomedical imaging applications, there are often subregions within the target where $\epsilon_r$ and $\sigma$ quite uniform; and it is only at the interfaces of the various anatomical structures where these properties experience the steepest gradients. Adaptive mesh techniques of the invention exploit this fact. In particular, during the iterative process, in regions where various objects are being resolved, the coarse mesh is modified to deploy a greater percentage of nodes in the areas where there appears to be the greatest variation in the $\epsilon_r$ and $\sigma$. See FIG. 6B, for example. As shown, the coarse mesh 160 has a high concentration in the region defined between GFDE; while other regions are less dense (note that a fine mesh is not illustrated in FIG. 6B). As the iterative process progresses, the mesh 160 eventually has its highest concentration of nodes in the areas of highest $\epsilon_r$ and $\sigma$ variation. This achieves better resolution in these areas without sacrificing the resolution in the more homogeneous regions.

Figure 7:
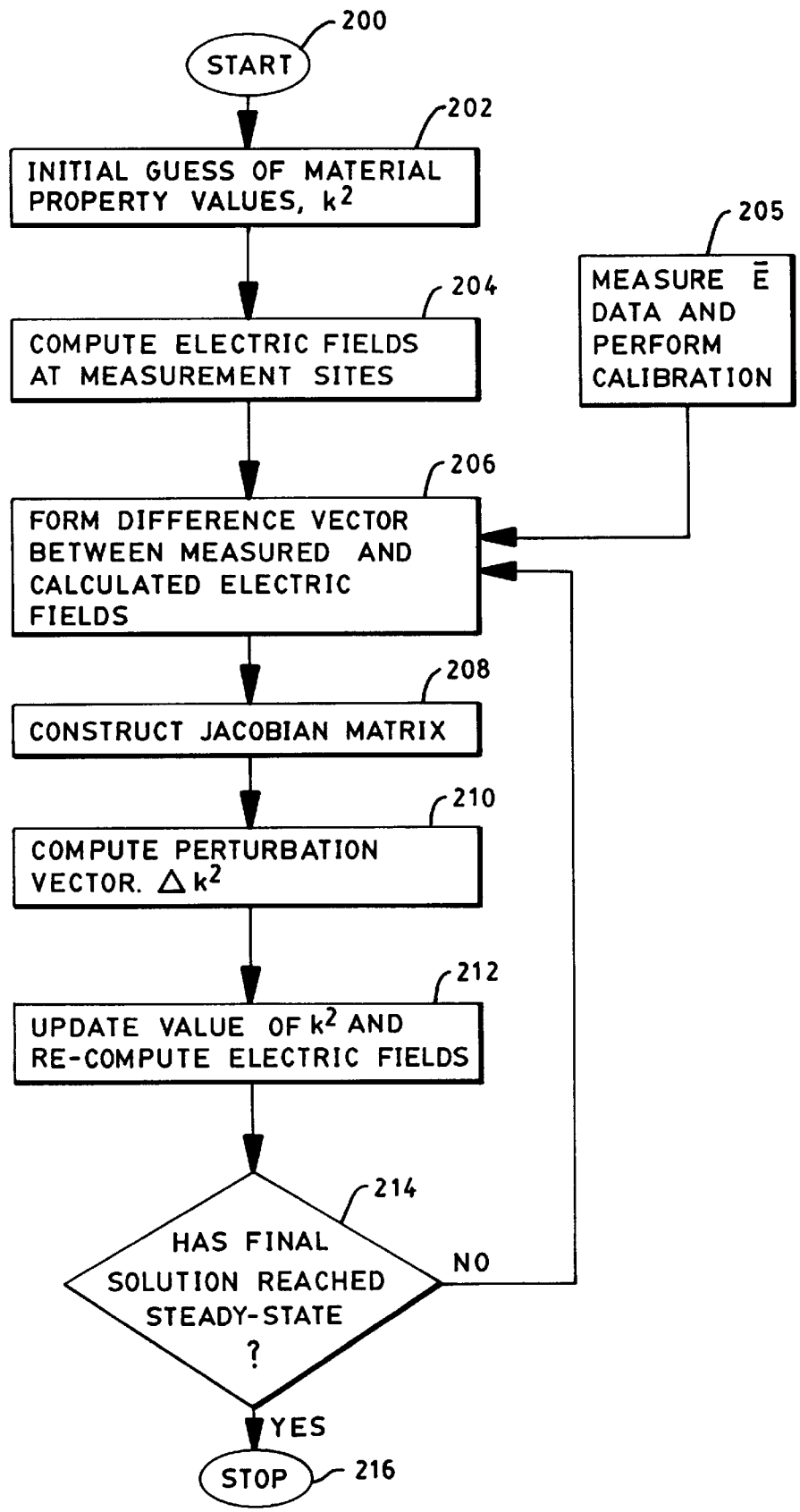
FIG. 7 shows a flow chart of the iterative process used to obtain microwave images, in accord with the invention.

FIG. 7 shows a flow chart that illustrates the iterative steps of acquiring microwave imaging in accord with the preferred embodiment of the invention. After the start 200, an initial estimate of material property values $\kappa^2$ is made at step 202. At step 204, the electric fields are computed at each of the measurement sites. At step 206, a difference vector is formed between the measured and calculated e-fields. At step 208, the Jacobian matrix is formed. At step 210, a perturbation vector $\Delta^2$ is formed. At step 212, the value of $\kappa^2$ is updated and the e-fields are re-computed. At step 214, the difference between the measured and calculated e-fields is evaluated relative to a predetermined, steady-state error function. If the difference is within the error function, the process is stopped at step 216. If not, however, the process is repeated at step 206.

The process of FIG. 7 is better understood in terms of the physics of a microwave system constructed according to the invention. By way of summary, a modulated signal is first transmitted from each transmitter on one side of the target region and received by a receiver antenna on the opposite side. This coherent signal is then down-converted to an intermediate frequency (IF) from which the relative phase and amplitudes are extracted. This process is done for all transmitter/receiver antenna combinations until a full complement of measurement data is collected. After calibration, these values are stored in the data acquisition computer and eventually transferred to the reconstruction computer for image processing.

The reconstruction of an image of the electrical properties is preferably performed using a Newton-Raphson iterative scheme. The numerical model computes electric field values at measurement sites within the homogeneous region (i.e., that region representing the illumination chamber surrounding a target area); while the target area has an unknown electrical property distribution. These computed values are then compared with the measured values from the data acquisition system and perturbations to this distribution are computed to improve the agreement between the actual and current calculated electrical property distributions. As the sets of measured electric field values and calculated electric field values approach one another, at each iteration, the actual and calculated electrical property distributions also converge.

In summary, the process of FIG. 7 can be described as follows:

1) At the first step 202, an initial guess is taken of the electrical property distribution, which is based on the coarse mesh discretization of the target region. Generally, the guess corresponds to a homogeneous distribution with values identical to the surrounding medium.

2) At step 204, the electric fields (at the operating frequency) are computed at the prescribed measurement sites for each of the desired transmitters. In certain embodiments illustrated above, 144 computations are made corresponding to 16 different transmitters with an associated 9 receiver antennas for each transmitter. This is a 2D calculation of the electric fields for the 2D TM propagation mode, and utilizes the modified hybrid element method of Appendix A. That is, the Boundary Element (BE) method is used to model the homogeneous area outside of the target region, and the Finite Element (FE) model is used to model the inhomogeneous area of the target region. These two representations are then coupled at their interface to allow for calculation of the electric fields at the desired locations on the mesh and outside the mesh.

3) At step 206, a difference vector between the measured and computed electric field is formed. The electrical fields are also measured and calibrated, in step 205, so that measured and calibrated e-field data is available for the several calculation steps 206, 208, 210, 212, and 214 and so that an image can be generated.

4) At step 208, a Jacobian matrix is formed where each entry is a sensitivity calculation of the change in the electric field at a measurement site due to a slight perturbation in the electrical property at a node in the coarse mesh. Note that the changes in the electric fields here are calculated on the fine mesh while the electrical properties are computed only at the nodes on the coarse mesh, with both meshes overlapping.

5) Using the difference vector from step 206 and the Jacobian matrix from step 208, an electrical property update vector, $\{\Delta\kappa^2\}$, is computed, at step 210. This update operates to move the current electrical property distribution closer to the actual distribution.

6) At step 212, the electrical property distribution is updated by the vector $\{\Delta\kappa^2\}$.

7) At step 214, the measured electric fields and the computed electric fields are compared. If the agreement between the two is sufficient (in a least squares sense), or the error function has reached a steady state, or some other metric, then the process ends, step 216, and the material distributions are written to a file and eventually displayed on a computer screen. If not, the process continues at step 206 in order to perturb the computed electrical property distribution such that it approaches the actual values.

Figure 8:
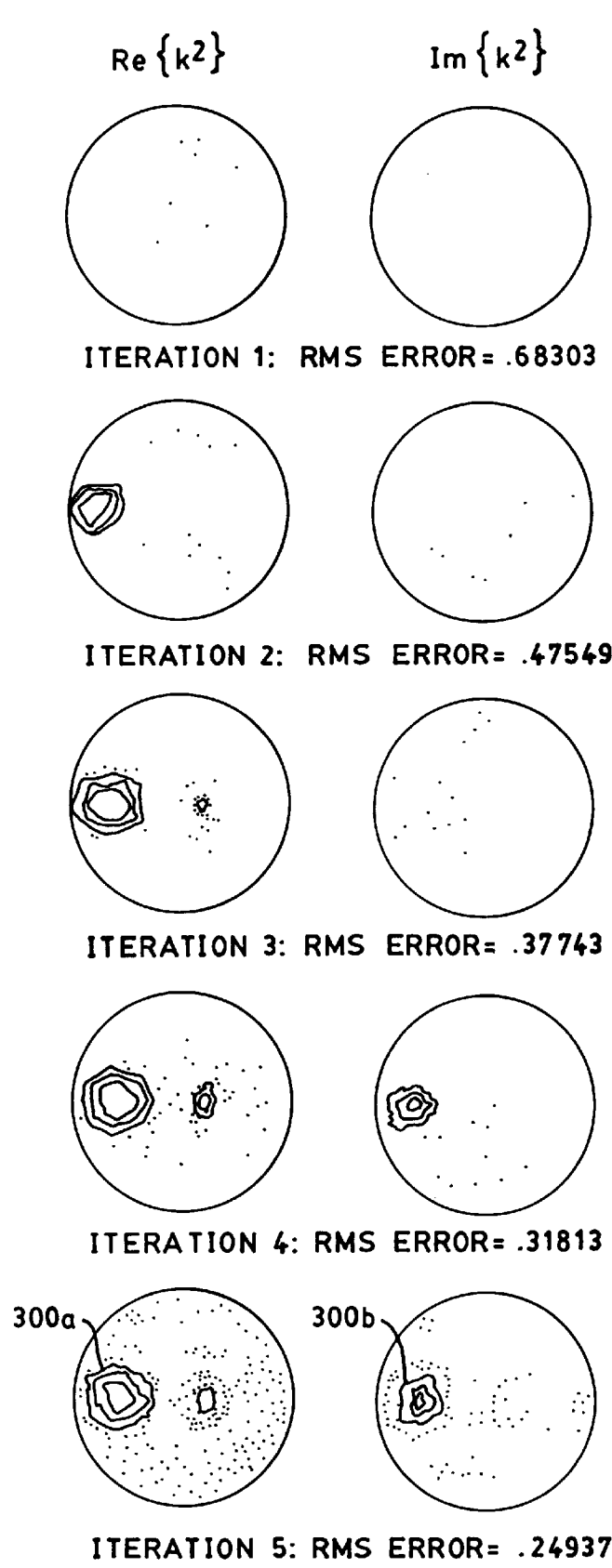
FIG. 8 illustrates actual data resolution and RMS error reduction achieved for an iterative sequence of image reconstruction such as in FIG. 7, in accord with the invention.

FIG. 8 shows exemplary data corresponding to the iterative processes described in connection with FIG. 7. Note that the process yields both real and imaginary components 300a, 300b, respectively (corresponding to $\epsilon_r$ and $\sigma$), and that the objects 300 become more pronounced through each iteration of reduced RMS error.

Figure 9:
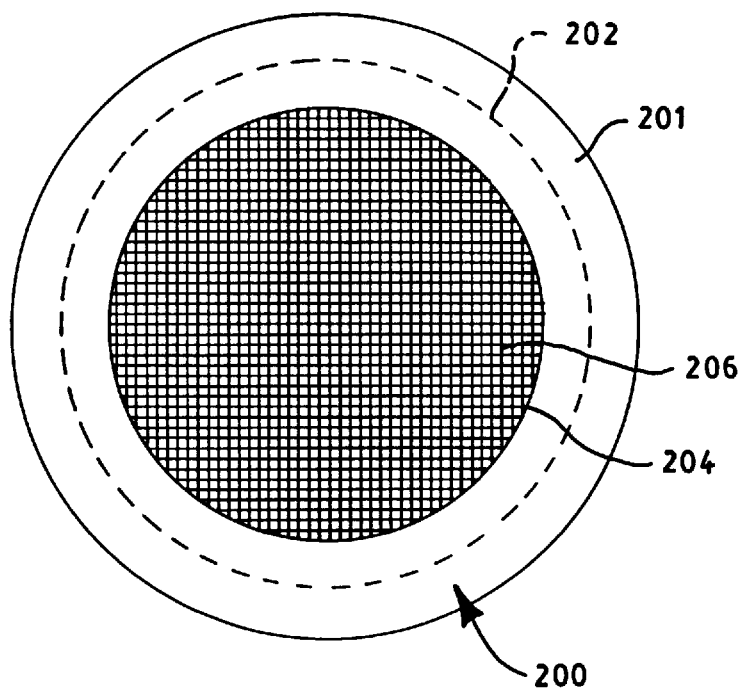
FIGS. 9 and 9A schematically illustrate hybrid element and dual mesh methodology of the invention.
Figure 9A:
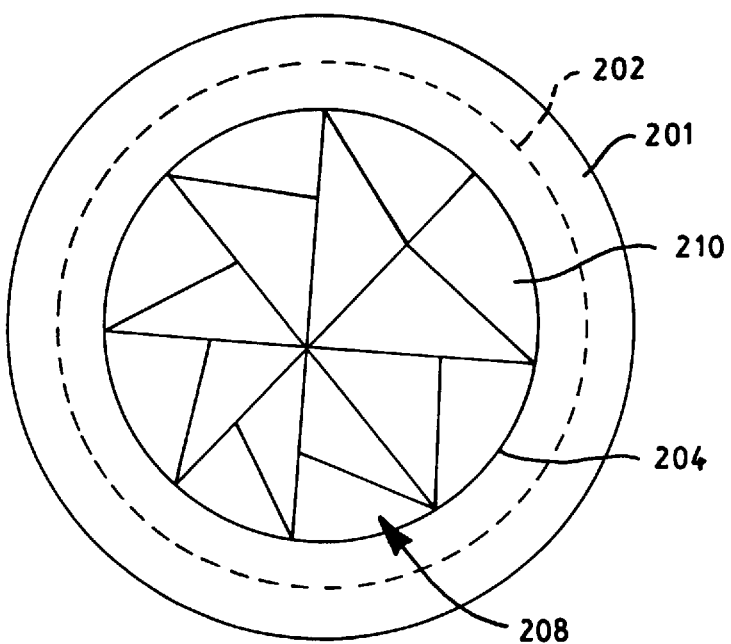

FIGS. 9 and 9A illustrate modified hybrid element and dual mesh methods as used with the invention. A chamber 200 with a plurality of antennas 202 are arranged about a target region 204 (note for clarity of illustration that the antennas 202 are shown as a single dotted line) which is discretized by a fine mesh corresponding to the selection of finite elements 206. From the antennas 202, many pieces of measurement data are acquired (e.g., for sixteen antennas, 144 measurements are acquired). The electric field is computed at each point on the fine mesh 206, and at several points outside the region 204, e.g., at the antenna locations 202 within the homogeneous chamber body 201 (that is, the chamber body 201 defines the fine mesh boundary and is assumed to have homogeneous $\epsilon_r$ and $\sigma$ electrical properties). Note that the fine mesh should be discretized at ten samples per wavelength, or better, and at seven samples per exponential decay, or better, in order to accurately define the electric field. The region 204 is then mathematically constructed to define a coarse mesh 208, FIG. 9A, where only the electrical properties, $\epsilon_r$ and $\sigma$ are of concern. The iterative processes described above, including the actual measurement of e-fields by the antennas 202, thereafter define the particular $\epsilon_r$ and $\sigma$ nodes 210 with greater and greater accuracy. Individual targets, i.e., "objects," are imaged within the region 204 at an accuracy defined by the coarse mesh.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and secured by Letters Patent is:

1. A method of determining electric field properties of an inhomogeneous target, comprising the steps of:

(A) measuring the electric field external to a boundary that defines the target;

(B) estimating electric property distributions on a coarse mesh discretization of the target; and (C) computing an electric field on a fine mesh discretization of the target, and at points external to the fine mesh discretization, the fine mesh having finer discretization than the coarse mesh and being overlapping with the coarse mesh.

2. A method according to claim 1, wherein the step of measuring the electric field comprises measuring the electric field at points within a homogeneous region external to the target.

3. A method according to claim 1, wherein the step of computing an electric field comprises modeling the points external as a boudary element representation.

4. A method according to claim 1, further comprising comparing the measured electric field with the computed electric field to determine a difference vector between measured and computed fields, the magnitude of the difference vector being compared against a predetermined accuracy.

5. A method according to claim 4, further comprising determining a least squares error of the difference vector.

6. A method according to claim 4, further comprising the step of computing a Jacobian matrix if the difference vector exceeds the predetermined accuracy, the matrix forming a sensitivity calculation relative to a change in the electric field at selected measurement sites due to a perturbation in the electric property distribution on the coarse mesh.

7. A method according to claim 6, further comprising the step of determining an electrical property update vector including solving a set of simultaneous equations defined by the Jacobian matrix and the difference vector between computed and measured electric fields.

8. A method according to claim 6, further comprising the step of computing an update vector of the electrical property distribution as a function of the difference vector and the Jacobian matrix.

9. A method according to claim 8, further comprising the steps of updating the electrical property distribution with the update vector and calculating an electric field as in step C with an updated electrical property distribution.

10. A method according to claim 9, further comprising calculating a least squared error between the measured electric field and the updated electric field.

11. A method according to claim 10, further comprising iteratively repeating the method, starting at step A, until the error is below an acceptable stopping criterion.

12. A method according to claim 1, wherein the step of computing the electric fields further comprises representing a region outside of the target as a homogeneous boundary element representation; representing the target as a plurality of inhomogeneous finite elements; and coupling the boundary element and finite element representations at the boundary to compute the electric fields.

13. A method according to claim 1, wherein the step of measuring the electric field further includes the steps of calibrating the measured electric field by (a) calculating a phase center of each antenna used to transmit an electromagnetic signal, and (b) modifying electric field amplitudes so as to convert 3-D data to a 2-D data format.

14. A method according to claim 13, wherein the step of calibrating the phase center of each antenna further comprises the step of measuring the electric field at a number of points within a uniform medium.

15. A method according to claim 13, wherein the step of calibrating the phase center of each antenna further comprises the step of utilizing a least squares approach to determine where the phase center must have been in order to generate the electric field.

16. A method according to claim 1, wherein the step of measuring the electric field comprises irradiating the target with electromagnetic energy from a first plurality of transmitting antennas that surround a first portion of the target, the microwave energy having a single operating frequency, receiving the electromagnetic energy at a second plurality of receive antennas for each of the transmitting antennas.

17. A method according to claim 16, wherein the receive antennas surround a second portion of the target and are arranged substantially within the same plane as the transmit antennas.

18. A method according to claim 1, wherein the step of computing the electrical field comprises simulating the electric field on the fine mesh at a number of nodes corresponding to a plurality of finite elements.

19. A method according to claim 1, wherein the step of computing the electrical field comprises simulating the electric field on the fine mesh at a spacing that is less than or equal to (a) 1/10th of a wavelength at the frequency of operation and (b) 1/7th of an exponential decay within the region discretized by finite elements.

20. A method according to claim 1, wherein the coarse mesh discretization is determined by the number of transmitting and receive antennas, the coarse mesh discretization having a number of nodes that are less than or equal to a multiplication between the number of transmitting antennas and the number of receive antennas.

21. A method according to claim 1, wherein the step of estimating electric property distributions comprises estimating the distributions based upon a homogeneous distribution with values identical to a medium surrounding the target.

22. A method according to claim 1, wherein the step of computing an electric field comprises computing a two-dimensional field utilizing hybrid element techniques.

23. A method according to claim 22, further comprising determining the electric field by a finite element discretization of the target while utilizing boudary elements to represent the surrounding region.

24. A method according to claim 23, wherein the step of discretizing the target comprises minimizing a number of nodes on the fine mesh so as to provide preselected electric field accuracy without excessive computing due to unnecessary mesh discretization beyond the target.

25. A method according to claim 1, wherein the step of computing an electric field comprises computing one of: a two-dimensional transverse magnetic electromagnetic propagation mode, a two-dimensional transverse electric electromagnetic propagation mode, and a three-dimensional electromagnetic propagation mode.

26. A method according to claim 1, wherein the step of estimating electric property distributions comprises estimating the distributions on triangular mesh nodes corresponding to the coarse mesh discretization.

27. A method according to claim 1, wherein the step of computing an electric field comprises computing the field on triangular mesh elements corresponding to the fine mesh discretization.

28. A method according to claim 1, wherein the step of computing an electric field comprises computing the field on triangular mesh elements corresponding to the fine mesh discretization, and wherein the step of estimating electric property distributions comprises estimating the distributions on triangular mesh elements corresponding to the coarse mesh discretization and such that a unit number of triangular mesh elements of the fine mesh fit within one triangular mesh element of the coarse mesh.

29. A method according to claim 1, further comprising utilizing parallel processing to process information for computing electric fields at a plurality of measurement sites for each of a plurality of transmitting antennas.

30. A method according to claim 1, further comprising the step of calculating the Jacobian matrix utilizing parallel processing to calculate sensitivities for electric field value changes at measurement sites with respect to perturbing the electric property distribution at each of the nodes on the coarse mesh.

31. A method according to claim 1, further comprising the step of adaptively modifying the coarse mesh so as to increase a density of nodes on the coarse mesh corresponding to sections of the target region with the greatest variation in $\epsilon_r$ and $\sigma$.

32. A system for imaging electrical properties of a target, comprising:

a chamber for surrounding the target and having an outer core that has substantially homogeneous electrical properties;

a plurality of antennas disposed within the core for transmitting and alternately receiving microwave energy within the range of about 300 Mhz to 1100 Mhz, initialization means for estimating the electrical property distribution of the target;

e-field computation means for computing an electric field at a fine mesh discretization of the target and at selected locations within the core;

e-field measurement means for measuring the electric field within the core;

difference vector means for determining a difference vector between the measured and computed electric fields;

Jacobian matrix means for forming a Jacobian matrix, each entry of the Jacobian matrix being a sensitivity calculation of the change in electric field at a measurement site due to a perturbation in the electrical property at a discretization node on a coarse mesh;

update vector means for determining an update vector as a function of the Jacobian matrix and the difference vector and for updating the electrical property distribution with the update vector; and comparing the measured and computed electric fields as a function of a predetermined metric.

* * * * *

UNITED STATES PATENT AND TRADEMARK OFFICE
CERTIFICATE OF CORRECTION

PATENT NO.   : 5,841,288
DATED        : November 24, 1998
INVENTOR(S)  : Paul M. Meaney et al.

It is certified that error appears in the above-identified patent and that said Letters Patent is hereby corrected as shown below:

Title page,
Item [56], References Cited, OTHER PUBLICATIONS,
"Paulsen et al." reference delete "pp. 1289-1303"and insert therefor -- pp. 1289-1304 --.
"Burdette et al," reference delete "pp. 38-49" and insert therefor -- pp. 38-50 --.
2nd "Paulsen et al." reference delete "pp. 209-288" and insert therefor -- pp. 209-228 --.

Column 1,
Line 40, delete "pp. 1735-30" and insert therefor -- pp. 1735-40 --.
Line 59, delete "pp. 531-536" and insert therefor -- pp. S31-S36 --.
Line 66, delete "Splinger-Verlag (1990)" and insert therefor -- Splinger-Verlag,
pp. 35-111 (1990) --.

Column 2,
Line 26, delete "pp. 860-974" and insert therfor -- pp. 860-874 --.
Line 33, delete "range" and insert therefor -- change --.
Line 35, delete "pp. 531-536" and insert therefor -- pp. S31-S36 --.

Column 9,
Line 22, delete "Hyperthermic" and insert therefor -- Hyperthermia --.
Line 23, delete "pp. 246-9" and insert therefor -- pp. 246-269 --.
Line 27, delete "pp. 1259-1304" and insert therefor -- pp. 1289-1304 --.

Column 11,
Line 17, delete "I, Q" and insert therefor --I & Q --.
Line 16, delete "51".
Line 17, delete "I, Q" and insert therefor-- I & Q --.
Line 18, delete "55" and insert therefor -- 35 --.

Column 14,
Line 10, delete "Hyperthermic" and insert therefor -- Hyperthermia --.
Line 11, delete "pp. 246-9" and insert therefor -- pp. 246-269 --.

UNITED STATES PATENT AND TRADEMARK OFFICE
CERTIFICATE OF CORRECTION

PATENT NO. : 5,841,288
DATED : November 24, 1998
INVENTOR(S) : Paul M. Meaney et al.

It is certified that error appears in the above-identified patent and that said Letters Patent is hereby corrected as shown below:

<u>Column 15,</u>
Line 49, delete "116".

<u>Column 18,</u>
Line 23, delete "$\Delta^2$" and insert therefor -- $\Delta k^2$ --.

<u>Column 20,</u>
Line 43, delete "boudary" and insert therefor -- boundary --.

Signed and Sealed this

Third Day of June, 2003

JAMES E. ROGAN
*Director of the United States Patent and Trademark Office*